(12) United States Patent
Benazet et al.

(10) Patent No.: US 9,206,177 B2
(45) Date of Patent: Dec. 8, 2015

(54) SUBSTITUTED DIMERIC QUINAZOLINE-2,4-DIONES AS FGF RECEPTOR AGONISTS

(71) Applicant: Sanofi, Paris (FR)

(72) Inventors: Alexandre Benazet, Paris (FR); Nathalie Guillo, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/369,144

(22) PCT Filed: Dec. 26, 2012

(86) PCT No.: PCT/IB2012/057726
§ 371 (c)(1),
(2) Date: Jun. 26, 2014

(87) PCT Pub. No.: WO2013/098763
PCT Pub. Date: Jul. 4, 2013

(65) Prior Publication Data
US 2014/0378483 A1 Dec. 25, 2014

(30) Foreign Application Priority Data
Dec. 28, 2011 (FR) ..................................... 11 62486

(51) Int. Cl.
A61K 31/517 (2006.01)
C07D 239/96 (2006.01)
C07D 471/04 (2006.01)
C07D 519/00 (2006.01)

(52) U.S. Cl.
CPC ............ C07D 471/04 (2013.01); C07D 519/00 (2013.01)

(58) Field of Classification Search
CPC ............................. A61K 31/217; C07D 239/96
USPC ....................... 514/266.31; 544/285; 548/453
See application file for complete search history.

(56) References Cited

FOREIGN PATENT DOCUMENTS

| WO | WO03084956 A1 | 10/2003 |
|---|---|---|
| WO | WO2007080325 A1 | 7/2007 |
| WO | WO2012004731 A1 | 1/2012 |
| WO | WO 2013/098763 | * 7/2013 |

OTHER PUBLICATIONS

Jordan, V. C. Nature Reviews: Drug Discovery, 2, 2003, 205.*
Hackam, et al. JAMA, 296(14), 2006, 1731-1732.*
Alavi, Alireza et al. (2003) Role of Raf in Vascular Protection from Distinct Apoptotic Stimuli, Science, vol. 301, pp. 94-96.
Andrade, Silvia et al.(1997) Sponge-Induced Angiogenesis in Mice and the Pharmacological Reactivity of the neovasculature Quantitated by a Fluorimetric Method, Microvascular Research 54, pp. 253-261.
Burger, Patricia et al. (2002) Fibroblast growth factor receptor-1 is expressed by endothelial progenitor cells, Blood, vol. 100, No. 10, pp. 3527-3535.
Ornitz et al. (2001) Review Fibroblast growth factors, Genome biology, vol. 2 No. 3, pp. 1-12.
Fibbi, G. et al (2002) Growth Factor-Dependent Proliferation and Invasion of Muscle Satellite Cells Require the Cell-Associated Fibrinolytic System, Biol. Chem, vol. 383, pp. 127-136, Walter de Gruyter, Berlin, N.Y.
Freedman, S.B. et al. (2001) Therapeutic Angiogenesis for Ischemic Cardiovascular Disease, J Mol Cell Cardiol, vol. 33, pp. 379-393.
Freedman, S.B. et al. (2002) Therapeutic Angiogenesis for Coronary Artery Disease, Ann. Intern. Med., vol. 136, pp. 54-71.
Hamacher, J. et al. (2002) Tumor Necrosis Factor -a and Angiostatin Are Mediators of Endothelial Cytotoxicity in Bronchoalveolar Lavages of patients with Acute Respiratory Distress Syndrome, American Journal of Respiratory and Critical Care Medicine, vol. 166, pp. 651-656.
Hendel, R. et al. (2000) Effect of Intracoronary Recombinant Human Vascular Endothelial Growth Factor on Myocardial Perfusion: Evidence for a Dose-Dependent Effect, Circulation, vol. 101, pp. 118-121.
Kawagushi, H. et al. (2001) Acceleration of Fracture Healing in Nonhuman Primates by Fibroblast Growth Factor-2, Journal of Clinical Endocrinology & Metabolism, vol. 86, No. 2, pp. 875-880.
Khurana, R. et al. (2003) Insights from Angiogenesis Trials Using Fibroblast Growth Factor for Advanced Arteriosclerotic Disease, Trends Cardiovasc Med, vol. 13, No. 3, pp. 116-122.
Klimaschewski, L. et al. (2004) Basic Fibroblast Growth Factor Isoforms Promote Axonal Elongation and Branching of Adult Sensory Neurons In Vitro, Neuroscience 126, pp. 347-353.
Koide, K. et al. (2001) A Synthetic Library of Cell-Permeable Molecules, Am. Chem. Soc., vol. 123, pp. 398-408.
Latham, RJ et al. (1999) Local Perivascular Delivery of Basic Fibroblast Growth Factor in Patients Undergoing Coronary Bypass Surgery: Results of a Phase I Randomized, Double-Blind, Placebo-Controlled Trial, Circulation, vol. 100, pp. 1865-1871, American Heart Association.
Latham, RJ et al. (2000) Intracoronary Basic Fibroblast Growth Factor (FGF-2) in Patients With Severe Ischemic Heart Disease: Results of a Phase I Open-Label Dose Escalation Study, Journal of the American College of Cardiology, vol. 36, No. 7, pp. 2132-0.

(Continued)

Primary Examiner — Douglas M Willis
(74) Attorney, Agent, or Firm — McDonnell Boehnen Hulbert & Berghoff LLP

(57) ABSTRACT

The invention relates to novel heterocyclic compounds which are pyrazolopyridine derivatives that induce FGFR dimerization, having the general formula: M-L-M2 in which M and M2, which may be identical or different, each represent, independently of one another, a monomer unit M and L represents a linker group which links $M_1$ and $M_2$ covalently with the monomer unit which follows (Formula M). Process for the preparation thereof and therapeutic use thereof.

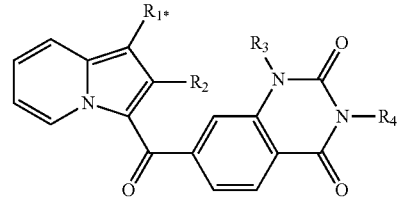

(M)

11 Claims, No Drawings

(56) References Cited

OTHER PUBLICATIONS

Lazarous, D. et al. (2000) Basic Fibroblast Growth Factor in Patients With Intermittent Claudication: Results of a Phase I Trial, Journal of the Am College of Cardiology, vol. 36, No. 4, pp. 1239-1244.

Neuhaus, P. et al. (2003) Reduced Mobility of Fibroblast Growth Factor (FGF)-Deficient Myoblasts Might Contribute to Dystrophic Changes in the Musculature of FGF2/FGF6/mdx Triple-Mutant Mice, Mol. Cell. Biol., vol. 23 (17), pp. 6037-6048.

Qureshi, S. et al. (1999) Mimicry of erythropoietin by a nonpeptide molecule, PNAS, vol. 96, No. 21, pp. 12156-12161.

Rydh-Rinder, M et al. (2001) Glutamate release from adult primary sensory neurons in culture is modulated by growth factors, Regulatory Peptides, vol. 102, pp. 69-79.

Sakurai, T et al. (2004) The efficient provascularization induced by fibroblast growth factor 2 with a collagen-coated device improves the cell survival of a bioartificial pancreas, Pancreas, vol. 28, No. 3, pp. e70-e79.

Seed, Brian (1994) Making agonists of antagonists, Chemistry & Biology, vol. 1, pp. 125-129.

Sherer, D et al. (2000) Antiogenesis during implantation, and placental and early embryonic development, Placenta, vol. 22, pp. 1-13.

Simons, M. et al. (2002) Pharmacological treatment of coronary artery disease with recombinant fibroblast growth factor-2: double-blind, randomized, controlled clinical trial, Circulation, vol. 105, pp. 788-793, American heart association.

Unger, E. et al. (2000) Effects of a single intracoronary injection of basic fibroblast growth factor in stable angina pectoris, Am J Cardiol, vol. 85, pp. 1414-1419.

Welm, BE (2002) Inducible dimerization of FGFR1: development of a mouse model to analyze progressive transformation of the mammary gland, The Journal of Cell Biology, vol. 157, No. 4, pp. 703-714.

Lee, C.K. (1989) J. Org. Chem, vol. 54, pp. 3744-3747.

Mitsuko, Kawano, et al. (2005) Comprehensive analysis of FGF and FGFR expression in skin: FGF18 is highly expressed in hair follicles and capable of inducing anagen from telogen stage hair follicles, Society for investigative dermatology, pp. 877-885.

Denner L, et al. "Antisense Oligonucleotides to Tenascin or FGFR1 Inhibit Restenosis in the Rat Carotid Angioplasty Model." Vascular Endothelium; Response to Injury (Cataravas, JD et al, eds.); NATO ASI Series, vol. 281, p. 269 (1996).

Francis DJ, et al. "Blockade of Vascular Smooth Muscle Cell Proliferation and Intimal Thickening After Balloon Injury by the Sulfated Oligosaccharide PI-88: Phosphomannopentaose Sulfate Directly Binds FGF-2, Blocks Cellular Signaling, and Inhibits Proliferation." Circulation Research. 92:e70-e77 (Apr. 10, 2003).

House SL, et al. "Fibroblast Growth Factor 2 Mediates Isoproterenol-induced Cardiac Hypertrophy through Activation of the Extracellular Regulated Kinase." Mol Cell Pharmacol; 2(4):143-154 (2010).

Kaye D, et al. "Role of transiently altered sarcolemmal membrane permeability and basic fibroblast growth factor release in the hypertrophic response of adult rat ventricular myocytes to increased mechanical activity in vitro." J Clin Invest; 97(2):281-91 (Jan. 15, 1996).

Kennedy SH, et al. "Basic FGF regulates interstitial collagenase gene expression in human smooth muscle cells." J Cell Biochem; 65(1):32-41 (Apr. 1997).

Lindner V and Reidy MA. "Proliferation of smooth muscle cells after vascular injury is inhibited by an antibody against basic fibroblast growth factor." Proc. Natl. Acad. Sci. USA; 88(9):3739-3743 (May 1, 1991).

Luo W, et al. "Inhibition of accelerated graft arteriosclerosis by gene transfer of soluble fibroblast growth factor receptor-1 in rat aortic transplants." Arterioscler Thromb Vasc Biol. 24(6):1081-6 (published online Apr. 8, 2004).

Pellieux C, et al. "Dilated cardiomyopathy and impaired cardiac hypertrophic response to angiotensin II in mice lacking FGF-2." J Clin Invest;108(12):1843-51 (Dec. 15, 2001).

Raj T, et al. "Inhibition of Fibroblast Growth Factor Receptor Signaling Attenuates Atherosclerosis in Apolipoprotein E-Deficient Mice." Arterioscler Thromb Vasc Biol; 26(8):1845-51 (published online May 18, 2006)s.

Segev A, et al. "Inhibition of vascular smooth muscle cell proliferation by a novel fibroblast growth factor receptor antagonist." Cardiovasc Res; 53(1):232-41 (Jan. 1, 2002).

\* cited by examiner

SUBSTITUTED DIMERIC QUINAZOLINE-2,4-DIONES AS FGF RECEPTOR AGONISTS

This application is a national stage application under 35 U.S.C. §371 of International Application No. PCT/IB2012/057726, filed Dec. 26, 2012, which claims priority to French Patent Application No. 1162486, filed Dec. 28, 2011, the disclosure of which are explicitly incorporated by reference herein.

BACKGROUND OF THE INVENTION

1. Field of the Invention

The subject of the present invention is novel heterocyclic compounds that induce fibroblast growth factor receptor (FGFR) dimerization, the process for the preparation thereof and the therapeutic uses thereof. The subject of the present invention is in particular novel compounds with a dimeric structure, as FGFR agonists.

2. Description of Related Art

FGFs are a family of polypeptides synthesized by a large number of cells during embryonic development and by cells of adult tissues under various pathological conditions.

FGF2 (or b-FGF) is the first and the most well-characterized of these growth factors. FGF2 is an 18 kDalton (kDa) protein which induces proliferation, migration and protease production by numerous cells, and in particular endothelial cells, fibroblasts, smooth muscle cells or alternatively bone cells. FGF2 interacts with the cells by means of two classes of receptors, high-affinity receptor tyrosine kinases (FGFRs) and low-affinity heparan sulphate proteoglycan (HSPG) type receptors located at the cell surface and in extracellular matrices. Thus, FGF2 and its receptors represent very relevant targets for therapies aimed at activating processes of angiogenesis, and of regeneration of smooth muscle cells, bone cells and hair-follicle cells.

Moreover, it is known that cell surface receptor tyrosine kinases transmit information through the plasma membrane particularly via mechanisms of dimerization of the extracellular domains of these receptors.

Known ligands capable of activating these dimerization mechanisms are typically natural compounds, such as FGFs, PDGF (Platelet-Derived Growth Factor), VEGF (Vascular Endothelial Growth Factor), EPO (Erythropoietin), G-CSF (Granulocyte-Colony Stimulating Factor), TPO (Thrombopoietin), certain cytokines or insulin.

B. Seed (*Chemistry and Biology*, November, 1994, 1, 125-129) puts forward the general principle that it would be possible to construct cell receptor agonists by dimerization of antagonists. However, there is no described example of a synthetic molecule constructed according to this concept. Articles such as S A. Qureshi (PNAS, 1999, vol 96, no 21, 12156-12161), B E. Welm (The Journal of cell biology, 2002, vol 157, 4, 703-714), K. Koide (J. Am. Chem. Soc., 2001, 123, 398-408) describe non-peptide compounds or chemical inducers of dimerization (CID), these compounds acting on chimeric receptors and not on natural receptors. They do not present any results showing that a CID makes it possible to activate the signalling pathway of a natural receptor.

In vertebrates, there are 22 members in the family of FGFs with a molecular weight ranging from 17 to 34 kDa and which share between 13% and 71% homology. These FGFs are highly conserved both at the gene level and at the amino acid sequence level. (D Ornitz. & N. Itoh, Fibroblast growth factors. Genome Biology, 30005.1-3005.12, 2001). FGFs interact with cells by means of high-affinity receptor tyrosine kinases (FGF-R1, —R2, —R3, —R4). The expression of FGFs suggests that they have an important role in development. Among the FGF family, FGF-2 is the FGF which has been most widely described. It is an 18 kDa protein which induces proliferation, migration and protease production on various cell types, such as endothelial cells, smooth muscle cells, fibroblasts, pericytes, osteoblasts or hair-follicle cells. Thus, the main therapeutic areas in which FGF2 is involved include neuronal and cardiovascular physiology, nerve regeneration, nociception, tissue repair, homoeostasis, and bone repair.

Thus, FGF2 and its receptors represent very relevant targets for therapies aimed at inducing angiogenesis and arteriogenesis processes (Khurana, R. & Simons, M. Insights from angiogenesis trials using fibroblast growth factor for advanced arteriosclerotic disease. Trends Cardiovasc Med 13, 116-22, 2003). When a blood vessel is obstructed, an ischaemic phase is observed, which induces a decrease in arterial circulation in an organ, thereby leading to a decrease in oxygen concentration in the damaged tissues. It has been shown in vitro and in vivo that several growth factors stimulate angiogenesis and arteriogenesis processes. FGF2 also induces neovascularization in vivo and also the development of collateral vessels after ligature of a vessel in pharmacological models.

Several pieces of evidence demonstrate that FGF2 is also involved in the differentiation of angioblasts into epithelial progenitor cells and thus participates in revascularization following occlusion (Burger, P. E. et al. Fibroblast growth factor receptor-1 is expressed by endothelial progenitor cells. Blood 100, 3527-35, 2002). Thus, strategies aimed at increasing the response of the cells of the vascular tree are suitable strategies for increasing post-ischaemic and in particular cardiac or coronary-artery revascularization (Freedman, S. B. & Isner, J. M. Therapeutic angiogenesis for ischemic cardiovascular disease. J Mol Cell Cardiol 33, 379-93, 2001; Freedman, S. B. & Isner, J. M. Therapeutic angiogenesis for coronary artery disease. Ann Intern Med 136, 54-71, 2002).

As regards the treatment of cardiac ischaemia, one of the most promising clinical trials is a trial in which FGF2 was sequestered in alginate microspheres in the presence of heparin (Laham, R. J. et al. Local perivascular delivery of basic fibroblast growth factor in patients undergoing coronary bypass surgery: results of a phase I randomized, double-blind, placebo-controlled trial. Circulation 100, 1865-71, 1999). After 90 days, all the patients treated with FGF2 showed no ischaemic cardiac symptom. In comparison, in the control group, 3 of the 7 patients had persistent symptoms at 90 days, and 2 patients had recourse to vascular surgery. Interestingly, the benefit of the therapy was maintained after 3 years of follow-up. Furthermore, three clinical trials on the injection of FGF2 into the coronary artery were carried out in the treatment of narrowing of the coronary arteries (Laham, R. J. et al. Intracoronary basic fibroblast growth factor (FGF-2) in patients with severe ischemic heart disease: results of a phase I open-label dose escalation study. J Am Coll Cardiol 36, 2132-9, 2000; Simons, M. et al. Pharmacological treatment of coronary artery disease with recombinant fibroblast growth factor-2: double-blind, randomized, controlled clinical trial. Circulation 105, 788-93, 2002; Unger, E. F. et al. Effects of a single intracoronary injection of basic fibroblast growth factor in stable angina pectoris. Am J Cardiol 85, 1414-9, 2000). The result of these three trials shows that intra-coronary infusions of FGF2 are well tolerated and significantly improve the clinical condition of the patients.

In another phase-I clinical trial, patients with peripheral artery disease leading to claudication received FGF2 injections (Lazarous, D. F. et al. Basic fibroblast growth factor in patients with intermittent claudication: results of a phase I trial. J Am Coll Cardiol 36, 1239-44, 2000). In this context, FGF2 was well tolerated in these patients and the clinical data suggest a beneficial effect of FGF2 in particular on improvement of walking in patients with peripheral disease, for instance Buerger's disease or thromboangiitis obliterans, which affects the distal vascular structures and which is characterized by distal arteritis in the legs, accompanied by pain and ulceration.

In another context requiring improved angiogenesis it has just been clearly demonstrated, in diabetic rats, that vascularization in bioartificial pancreases was much greater when the pancreases were impregnated with microspheres carrying FGF2 (Sakurai, Tomonori; Satake, Akira, Sumi, Shoichiro, Inoue, Kazutomo, Nagata, Natsuki, Tabata, Yasuhiko. The Efficient Prevascularization Induced by Fibroblast Growth Factor 2 With a Collagen-Coated Device Improves the Cell Survival of a Bioartificial Pancreas. Pancreas. 28(3):e70-e79, April 2004). This revascularization thus improves the survival of the implanted bioartificial pancreases and, consequently, the survival of the graft. Thus, FGFs appear to contribute to improving bioartificial pancreatic graft survival in diabetic patients and, more generally, appear to contribute to improving graft revascularization and appear to be involved in graft survival.

In addition to the angiogenesis-inducing effects, FGF2 protects endothelial cells against inducers of apoptosis. It has now been clearly described that FGF2 is an endothelial cell survival factor (Role of Raf in Vascular Protection from Distinct Apoptotic Stimuli: A Alavi, J. D. Hood, R. Frausto, D. G. Stupack, D. A. Cheresh: Science 4 Jul. 2003: Vol. 301. no. 5629, pp. 94-96). Acute respiratory distress syndrome (ARDS) is characterized by cardiovascular and neuropsychiatric problems. In the context of the cardiovascular problems, patients exhibit considerable vascular damage and in particular a high level of induction of endothelial cell apoptosis. Recently, Hamacher et al. have demonstrated that bronchoalveolar lavage fluids from patients suffering from ARDS exhibit pro-apoptotic activity against lung microvascular endothelial cells (Tumor necrosis factor-alpha and angiostatin are mediators of endothelial cytotoxicity in bronchoalveolar lavages of patients with acute respiratory distress syndrome. Am J Respir Crit. Care Med. 2002 Sep. 1; 166(5):651-6: Hamacher J, Lucas R, Lijnen H R, Buschke S, Dunant Y, Wendel A, Grau G E, Suter P M, Ricou B.).

Pre-eclampsia is a pathological condition of the placenta which is associated with a deficiency in vascularization (Sherer, D. M. & Abulafia, O. Angiogenesis during implantation, and placental and early embryonic development. Placenta 22, 1-13, 2001). These deficiencies in vascularization are thought to be due to a deficiency in angiogenesis and to lead to disruptions at the level of the placenta that can result in death of the foetus.

Healing is a tissue regeneration process which does not require treatment in most cases. However, complications can occur, such as infection or the appearance of a keloid scar, which is a pathological scar characterized by a fold of fibrous consistency, or by skin retractions resulting in a loss of elasticity of the skin. The healing phase takes place in 5 stages: The first phase is the inflammatory phase, which is the starting point for the tissue repair. This inflammatory reaction causes vasodilation and increases the permeability of the lesion. The second phase is the angiogenesis phase, which enables the provision of nutrients and oxygen, essential to the cells. The third phase is the migration phase: the renewal (and therefore granulation) tissue is put in place: this is the beginning of the production of the scar. All the connective tissue cells migrate to the centre of the lesion, in particular the fibroblasts and the keratinocytes. The fourth phase is the proliferation phase, which consists of a massive proliferation of the connective tissue cells, and of fibres associated with blood vessel development. The final phase is the maturation phase, which is the longest phase: it lasts from 18 to 24 days. The number of fibroblasts will then decrease, as will the number of blood vessels, so as to result in the end of healing. In the case of diabetic patients, healing is a slow and difficult process which exposes them to chronic wounds that are extremely difficult to heal, often becoming complicated by infectious phenomena which can secondarily lead to amputations. By virtue of their pleiotropic activities, FGFs participate in tissue repair in particular by activating keratinocytes and fibroblasts and by participating in the angiogenesis phenomenon. Thus, FGFs appear to play a role in improving healing in healthy or diabetic patients, both from the point of view of the rapidity of healing and from the point of view of scar quality. It has also been clearly described that the levels of growth factors involved in healing phenomena, and in particular FGFs, decrease very greatly with age. Thus, in elderly patients, the deficiencies and delays in healing are linked to deficiencies in FGFs in the skin.

Glutamate is a putative transmitter of dorsal ganglion neurons and bradykinin is a molecule produced during inflamation that can activate and sensitize nociceptive fibres. In this context, FGF2 could modulate inflammatory pain even though no regulatory effect of FGF2 on nociceptive fibres has been demonstrated in vivo. However, it has been demonstrated that FGF2 completely blocks bradykinin-stimulated glutamate release in vitro (Rydh-Rinder et al. (2001) Regul Pept 102:69-79). Thus, FGFs could play a role in nociception and chronic pain.

Peripheral neuropathy is an axonal or demyelinating attack on the motor and/or sensory peripheral nerve that leads to desensitization of the distal limbs. One of the consequences of the nerve damage may be a perforating ulcer, which is to be particularly feared when there is considerable damage to the profound sensitivity since, in this case, the body's weight has a tendency to always be carried by the same support points. One of the major secondary complications of diabetes is the chronic development of peripheral neuropathy. In this context, it has been demonstrated that FGF2 induces axonal regeneration that could be a therapy of choice in the treatment of peripheral nerve damage and therefore in peripheral neuropathy (Basic fibroblast growth factor isoforms promote axonal elongation and branching of adult sensory neurons in vitro. Klimaschewski L, Nindl W, Feurle J, Kavakebi P, Kostron H. Neuroscience. 2004; 126(2):347-53).

It has been proposed that the FGF system is an essential system of muscle regeneration, and of myoblast survival and proliferation (Neuhaus, P. et al. Reduced mobility of fibroblast growth factor (FGF)-deficient myoblasts might contribute to dystrophic changes in the musculature of FGF2/FGF6/mdx triple-mutant mice. Mol Cell Biol 23, 6037-48, 2003). FGF2 could be exploited in order to promote muscle regeneration, in particular in the case of sarcopenia, of loss of smooth-muscle functionality in the sphincters, and also for the survival and progression of transplanted myoblasts, and in particular in Duchenne muscular dystrophy. Growth factors such as VEGF or FGF2 also appeared to improve myocardial perfusion after ischaemia (Hendel, R. C. et al. Effect of intracoronary recombinant human vascular endothelial growth factor on myocardial perfusion: evidence for a dose-dependent effect. Circulation 101, 118-21, 2000). Furthermore, the vascular network is essential to tissue development and preservation. By promoting the delivery of nutrients, oxygen and cells, the blood vessels assist in maintaining the functional and structural integrity of tissues. In this context, angiogenesis and vasculogenesis make it possible to preserve and perfuse tissues after ischaemia. Angiogenic growth factors such as FGF2 thus promote revascularization for tissue regeneration. Thus, FGF2, by acting directly on skeletal muscle cells and on angiogenesis, would have an effect on the regeneration of dystrophic or normal muscles (Fibbi, G., D'Alessio, S., Pucci, M., Cerletti, M. & Del Rosso, M. Growth factor-dependent proliferation and invasion of muscle satellite cells require the cell-associated fibrinolytic system. Biol Chem 383, 127-36, 2002).

Among the main growth factors, it is now clearly established that systemic administration of FGF2 facilitates bone repair after fracture (Acceleration of fracture healing in non-human primates by fibroblast growth factor-2. Kawaguchi H, Nakamura K, Tabata Y, Ikada Y, Aoyama I, Anzai J, Nakamura T, Hiyama Y, Tamura M. J Clin Endocrinol Metab. 2001 February; 86(2), 875-880). The local application of FGF2 in gelatin matrices accelerates bone repair in primates, suggesting the clinical usefulness of FGF2 in the treatment of fractures.

The endogenous overregulation of FGF7 (or KGF) and of FGF18 appears to be an important mechanism for promoting the proliferation, migration and protection of hair follicles in pathological cases or following treatment with a cytotoxic agent (Comprehensive Analysis of FGF and FGFR Expression in Skin: FGF18 Is Highly Expressed in Hair Follicles and Capable of Inducing Anagen from Telogen Stage Hair Follicles. Mitsuko Kawano, Akiko Komi-Kuramochi, Masahiro Asada, Masashi Suzuki, Junko Oki, Ju Jiang and Toru Imamura).

BRIEF SUMMARY OF THE INVENTION

The applicant has now found novel synthetic molecules capable of inducing FGF receptor dimerization and which can be of use in numerous mechanisms where FGFRs are involved, such as angiogenesis, or smooth muscle, bone or hair-follicle cell regeneration.

The objective of the invention is to propose novel FGF receptor agonist compounds with a dimeric structure.

These compounds bring about dimerization of FGF receptors, which causes their activation and, in the end, cell activation.

A subject of the present invention is FGF receptor agonist compounds corresponding to the general formula:

$$M_1\text{-}L\text{-}M_2$$

in which $M_1$ and $M_2$, which may be identical or different, each represent, independently of one another, a monomer unit M and L represents a linker group which links $M_1$ and $M_2$ covalently.

The agonists of formula $M_1$-L-$M_2$ according to the invention comprise two monomer units of general formula M, called $M_1$ and $M_2$, which may be identical or different, chosen as each having an FGFR antagonist activity.

A subject of the present invention is FGF receptor agonist compounds as defined above, characterized in that said monomer unit corresponds to the general formula M which follows:

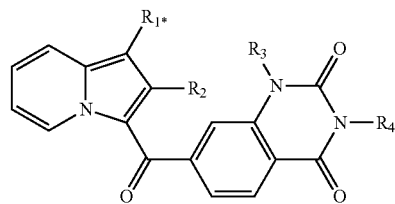

in which,

\* indicates the site of linkage between the monomer unit M and the linker L, $R_1$ represents a group —NHCOPh, said phenyl being substituted with an oxygen atom, such that the oxygen atom is the site of linkage between the monomer unit and the linker L; this group can be denoted —NHCOPhO\*, or an aryl, in particular phenyl, group or a heteroaryl group, said group being optionally substituted with a group chosen from a divalent oxygen atom, such that the oxygen atom is the site of linkage between the monomer unit M and the linker L, or an amide group —CONH\*—, such that the nitrogen atom is the site of linkage between the monomer unit and the linker L, $R_2$ represents an alkyl, advantageously a methyl group, $R_3$ represents a hydrogen atom or a linear, branched, cyclic or partially cyclic alkyl group, $R_4$ represents a hydrogen atom or an alkyl or -alkyl-COOR$_5$ group with $R_5$ representing a hydrogen atom or an alkyl group, in the form of a base or of an addition salt with an acid or with a base.

DETAILED DESCRIPTION OF THE INVENTION

L represents a linker group which links $M_1$ and $M_2$ covalently in such a way that the distance between the two monomer units $M_1$ and $M_2$ allows the dimerization of two FGF receptors. Said linker group comprises from 1 to 25 links. Said linker group L more particularly comprises from 11 to 20 links. The term "links" is intended to mean only the bonds between atoms which make it possible to connect the monomer units $M_1$ and $M_2$.

The linker group L is characterized by a flexibility which enables each monomer unit of the compound of formula $M_1$-L-$M_2$ to establish contact with the extracellular binding sites of the FGFR transmembrane receptors.

L is attached, firstly, to a monomer unit of formula $M_1$ by an atom placed on the substituent $R_1$ and attached, secondly, to the other monomer unit of formula $M_2$ by an atom placed on the substituent $R_1$, with $M_1$ and $M_2$ being identical or different.

The subject of a subgroup according to the present invention is more particularly compounds as defined above, characterized in that L connects the 2 monomer units $M_1$ and $M_2$ via the radical $R_1$.

The connecting atoms which are located on the substituent $R_1$ of the monomer unit of formula M can be represented by oxygen or nitrogen atoms.

The junctions between L and the monomer units can be represented by C—O or C—N bonds.

The linker groups L suitable for the invention can be chosen from structures of the type such as alkyl radicals which may be linear or branched and optionally interrupted with one or more heteroatoms, such as oxygen, nitrogen and/or phosphorus, one or more rings, one or more heterocycloalkyls (such as piperazine), or one or more aryls (such as phenyl) or heteroaryls (such as pyridine).

The linker groups L can optionally comprise one or more functions such as amide, amine, ether and/or phosphodiester.

The branches in the linker group L may themselves comprise alkyl radicals which may be linear or branched and optionally interrupted with one or more heteroatoms, such as oxygen and/or nitrogen, one or more heterocycloalkyls, one or more aryls or heteroaryls, and/or optionally one or more functions such as amide, amine, ether, phosphate, sulphate and/or hydroxyl.

These compounds of formula $M_1$-L-$M_2$ can exist in the form of bases or in a form salified with acids or bases, in particular pharmaceutically acceptable acids or bases. Such addition salts are part of the invention. Mention may in particular be made of D,L-lysine salts or sodium salts.

In the context of the present invention, and unless otherwise mentioned in the text:

- the term alkyl is intended to mean: a linear or branched, and saturated, hydrocarbon-based aliphatic group comprising from 1 to 4 carbon atoms; by way of examples, mention may be made of methyl, ethyl, propyl and pentyl groups;
- the term heterocycloalkyl is intended to mean: a cyclic alkyl group comprising from 3 to 8 members, comprising between 3 and 6 carbon atoms and optionally comprising one or more heteroatoms, for example 1 or 2 heteroatoms, such as nitrogen and/or oxygen, said cycloalkyl group being optionally substituted with one or more halogen atoms and/or alkyl groups. By way of examples, mention may be made of cyclopropyl, cyclopentyl, piperazinyl, pyrrolidinyl and piperidinyl groups;
- the term halogen is intended to mean: a chlorine, fluorine, bromine or iodine atom;
- the term haloalkyl is intended to mean: an alkyl chain in which all or some of the hydrogen atoms are replaced with halogen atoms, such as fluorine atoms;
- the term aryl is intended to mean: a cyclic aromatic group comprising between 5 and 10 carbon atoms, for example a phenyl group; and
- the term heteroaryl is intended to mean: a cyclic aromatic group comprising between 3 and 10 atoms, including one or more heteroatoms, for example between 1 and 4 heteroatoms, such as nitrogen or oxygen, this group comprising one or more, preferably 1 or 2, rings. The heteroaryls are optionally substituted with one or more alkyl groups or an oxygen atom. By way of examples, mention may be made of thienyl, pyridinyl, pyrazolyl, imidazolyl and triazolyl groups.

The subject of a subgroup according to the present invention is more particularly FGF receptor agonist compounds as defined above, characterized in that said monomer unit corresponds to the general formula M which follows:

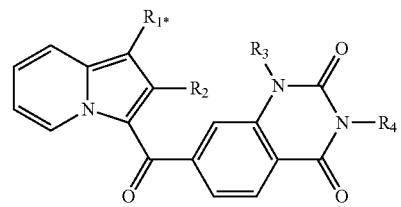

in which,

*indicates the site of linkage between the monomer unit M and the linker L, $R_1$ represents a group —NHCOPh, said phenyl being substituted with an oxygen atom, such that the oxygen atom is the site of linkage between the monomer and the linker L; this group can be denoted —NHCOPhO*, or a phenyl group, said group being optionally substituted with a group chosen from a divalent oxygen atom, such that the oxygen atom is the site of linkage between the monomer unit M and the linker L, or an amide group —CONH*—, such that the nitrogen atom is the site of linkage between the monomer unit and the linker L, $R_2$ represents a methyl group, $R_3$ represents a hydrogen atom, $R_4$ represents an -alkyl-COO$R_5$ group with $R_5$ representing a hydrogen atom, in the form of a base or of an addition salt with an acid or a base.

The subject of another subgroup according to the invention is particularly compounds as defined above, comprising the monomer unit of formula M in which:

$R_1$ represents an —NHCO-PhO*, -Ph-O* or -Ph-NHCO* group, in the form of a base or of an addition salt with an acid or with a base.

The subject of another subgroup according to the invention is particularly compounds as defined above, comprising the monomer unit of formula M in which:

$R_1$ represents an —NHCO-PhO*, -Ph-O* or -Ph-NHCO* group, $R_2$ represents a methyl group, in the form of a base or of an addition salt with an acid or with a base.

The subject of another subgroup according to the invention is particularly compounds as defined previously, comprising the monomer unit of formula M in which:

$R_3$ represents a hydrogen atom, $R_4$ represents an -alkyl-COO$R_5$ group with $R_5$ representing a hydrogen atom or an alkyl group, in particular a hydrogen atom, in the form of a base or of an addition salt with an acid or a base.

The subject of another subgroup according to the invention is more particularly compounds of formula $M_1$-L-$M_2$ as defined previously, with $M_1$ identical to $M_2$.

The linker groups L can be more particularly chosen from the radicals having the following formulae:

(A) 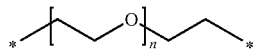

(B) 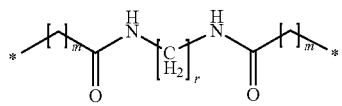

(C) 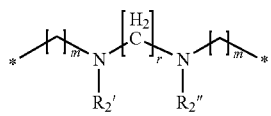

(D) 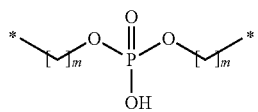

(E) 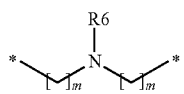

in which
* indicates the atom for connecting L with the monomer unit M on the substituent $R_1$,
n represents an integer from 0 to 5,
m represents an integer from 1 to 5,
r represents an integer from 1 to 6,
$R_2'$ and $R_2''$, which may be identical or different, represent a linear alkyl radical having from 1 to 5 carbon atoms, and which can be optionally linked to form a ring,
$R_6$ represents a $(C_1-C_4)$alkyl group, preferably a $—(C_1-C_2)$alkyl group, optionally substituted with one or more substituents chosen from:
- an aryl or heteroaryl group optionally substituted with a group chosen from a hydroxyl, amine or $NR_6'R_6''$ group with $R_6'$ and $R_6''$, which may be identical or different, chosen from a hydrogen atom or a linear, branched or cyclic $(C_1-C_4)$alkyl group,
- a heterocycloalkyl group comprising at least one heteroatom chosen from a nitrogen atom and an oxygen atom optionally substituted with a linear or branched alkyl group,
- an $NR_6'R_6''$ group with $R_6'$ and $R_6''$, which may be identical or different, chosen from a hydrogen atom or a linear, branched or cyclic $(C_1-C_4)$alkyl group,
- an $O—(C_1-C_4)$alkyl group optionally substituted with a hydroxyl group, in the form of a base or of an addition salt with an acid.

The subject of another subgroup according to the invention is the linker groups L having the formulae above in which:
* indicates the atom for connecting L with the monomer unit M on the substituent $R_1$,
n represents 2 or 3,
m represents 1, 2, 3 or 5,
r represents 2, 4 or 6,
$R_2'$ and $R_2''$, which may be identical or different, represent a linear alkyl radical having from 1 to 5 carbon atoms, and which can be optionally linked to form a ring,
$R_6$ represents a $—(C_1-C_4)$alkyl group, preferably a $—(C_1-C_2)$alkyl group, optionally substituted with one or more substituents chosen from:
- an aryl or pyridine group optionally substituted with an $NR_6'R_6''$ group with $R_6'$ and $R_6''$, which may be identical or different, representing a linear $(C_1-C_4)$alkyl group,
- a heterocycloalkyl group comprising at least one heteroatom chosen from a nitrogen atom and an oxygen atom optionally substituted with a linear or branched alkyl group,
- an $NR_6'R_6''$ group with $R_6'$ and $R_6''$, which may be identical or different, representing a linear $—(C_1-C_4)$alkyl group,
- an $O—(C_1-C_4)$alkyl group optionally substituted with a hydroxyl group, in the form of a base or of an addition salt with an acid.

The subject of another subgroup according to the invention is particularly compounds as defined above, such that the linker group L is the radical A, in the form of a base or of an addition salt with an acid or a base.

The subject of another subgroup according to the invention is particularly compounds as defined above, such that the linker group L is the radical B, in the form of a base or of an addition salt with an acid or a base.

The subject of another subgroup according to the invention is particularly compounds as defined above, such that the linker group L is the radical C, in the form of a base or of an addition salt with an acid or a base.

The subject of another subgroup according to the invention is particularly compounds as defined above, such that the linker group L is the radical D, in the form of a base or of an addition salt with an acid or a base.

The subject of another subgroup according to the invention is particularly compounds as defined above, such that the linker group L is the radical E, in the form of a base or of an addition salt with an acid or a base.

The subgroups defined above, taken separately or in combination, also form part of the invention.

Among the compounds of the invention, mention may in particular be made of the following compounds:

Compound 1: 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid;

Compound 2: 2,2'-{oxybis[ethane-2,1-diyloxyethane-2,1-diyloxybenzene-3,1-diyl(2-methylindolizine-1,3-diyl)carbonyl(2,4-dioxo-1,4-dihydroquinazoline-6,3(2H)-diyl)]}diacetic acid;

Compound 3: 2,2'-{ethane-1,2-diylbis[oxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid;

Compound 4: 2,2'-{hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid;

Compound 5: 2,2'-{butane-1,4-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid;

Compound 6: 2,2'-{hexane-1,6-diylbis[imino(2-oxoethane-2,1-diyloxybenzene-3,1-diyl(2-methylindolizine-1,3-diyl)carbonyl(2,4-dioxo-1,4-dihydroquinazoline-6,3(2H)-diyl)]}diacetic acid;

Compound 7: 2,2'-{butane-1,4-diylbis[imino(2-oxoethane-2,1-diyloxybenzene-3,1-diyl(2-methylindolizine-1,3-diyl)carbonyl(2,4-dioxo-1,4-dihydroquinazoline-6,3(2H)-diyl)]}diacetic acid;

Compound 8: 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

Compound 9: 2,2'-{(ethylimino)bis[pentane-5,1-diyloxybenzene-4,1-diyl(2-methylindolizine-1,3-diyl)carbonyl(2,4-dioxo-1,4-dihydroquinazoline-7,3(2H)-diyl)]}diacetic acid;

Compound 10: 2,2'-({[2-(morpholin-4-yl)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

Compound 11: 2,2'-({[2-(4-methylpiperazin-1-yl)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

Compound 12: 2,2'-{[(pyridin-4-ylmethyl)imino]bis[pentane-5,1-diyloxybenzene-4,1-diyl(2-methylindolizine-1,3-diyl)carbonyl(2,4-dioxo-1,4-dihydroquinazoline-7,3(2H)-diyl)]}diacetic acid;

Compound 13: 2,2'-({[4-(dimethylamino)benzyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

Compound 14: 2,2'-({[2-(diethylamino)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

Compound 15: 2,2'-{piperazine-1,4-diylbis[propane-3,1-diyloxybenzene-4,1-diyl(2-methylindolizine-1,3-diyl)carbonyl(2,4-dioxo-1,4-dihydroquinazoline-7,3(2H)-diyl)]}diacetic acid;

Compound 16: [7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4$\lambda^5$-phosphanon-1-yl}carbamoyl)phenyl]-2-methylindolizin-3-yl}carbonyl)-2,4-dioxo-1,4-dihydroquinazolin-3(2H)-yl]acetic acid;

Compound 17: 2,2'-{ethane-1,2-diylbis[oxyethane-2,1-diylcarbamoylbenzene-4,1-diyl(2-methylindolizine-1,3-diyl)carbonyl(2,4-dioxo-1,4-dihydroquinazoline-7,3(2H)-diyl)]}diacetic acid;

Compound 18: 2,2'-{ethane-1,2-diylbis[oxyethane-2,1-diylcarbamoylbenzene-3,1-diyl(2-methylindolizine-1,3-diyl)carbonyl(2,4-dioxo-1,4-dihydroquinazoline-7,3(2H)-diyl)]}diacetic acid;

Compound 19: [7-({1-[3-({9-[3-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4$\lambda^5$-phosphanon-1-yl}carbamoyl)phenyl]-2-methylindolizin-3-yl}carbonyl)-2,4-dioxo-1,4-dihydroquinazolin-3(2H)-yl]acetic acid;

Compound 20: 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetic acid.

It should be noted that the compounds above were named using IUPAC nomenclature by means of the ACDLABS 10.0 ACD/name (Advanced Chemistry development) or AutoNom (Beilstein Informations system) software.

In what follows, the term "protective group (PG)" is intended to mean a group which makes it possible, firstly, to protect a reactive function such as a hydroxyl or an amine during a synthesis and, secondly, to regenerate the intact reactive function at the end of synthesis. Examples of protective groups and also methods of protection and of deprotection are given in <<Protective Groups in Organic Synthesis>>, Green et al., 4th Edition (John Wiley & Sons, Inc., New York).

In what follows, the term "leaving group (LG)" is intended to mean a group which can be easily cleaved from a molecule by breaking a heterolytic bond, with the departure of a pair of electrons. This group can thus be easily replaced with another group in a substitution reaction, for example. Such leaving groups are, for example, halogens or an activated hydroxyl group, such as a mesyl, tosyl, triflate, acetyl, etc. Examples of leaving groups and also the references for preparing them are given in <<Advanced Organic Chemistry>>, J. March, 5th Edition, Wiley Interscience, p. 310-316.

In accordance with the invention, the compounds of general formula (I) can be prepared according to the process which follows.

Preparation of the Monomer Units

Scheme 1:
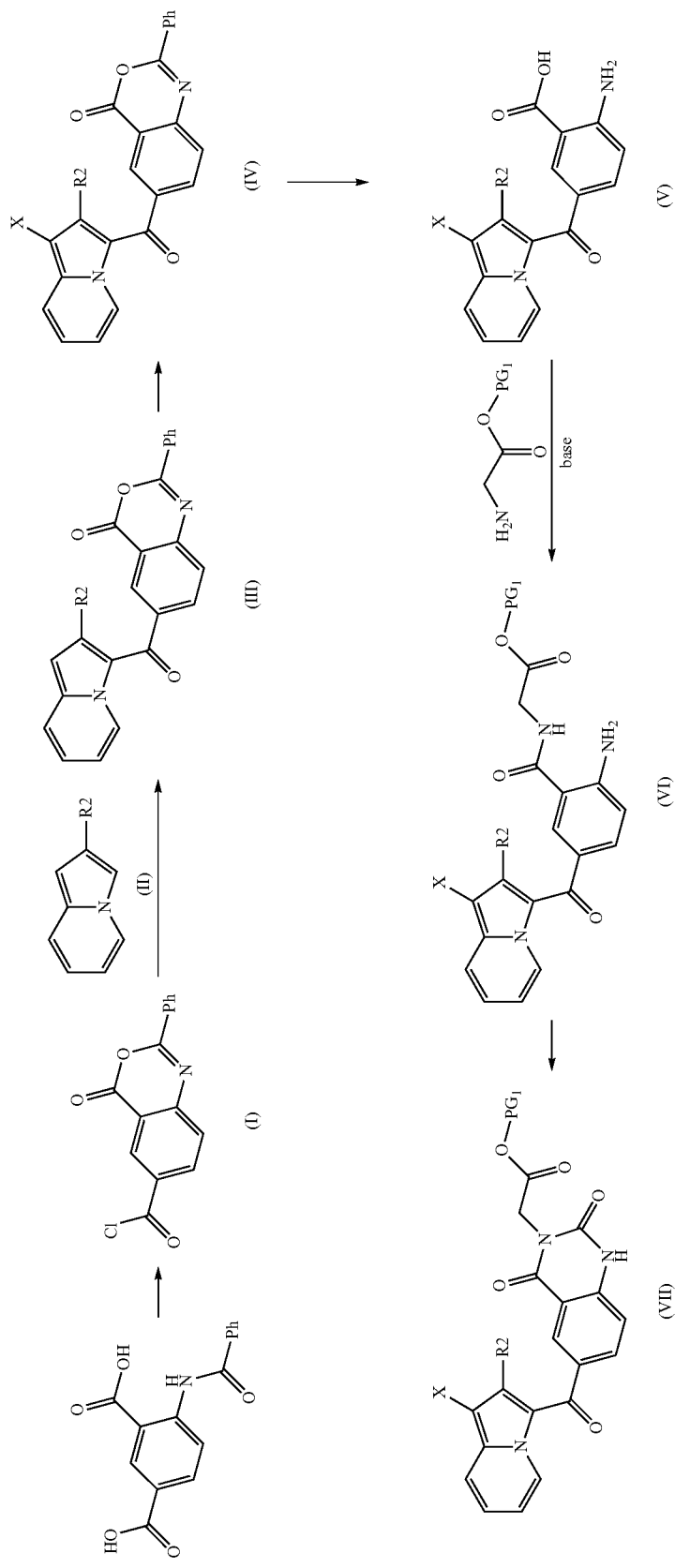

Scheme 1 illustrates the synthesis of the monomer units of formula (VII). The acid chloride of formula (I) is obtained from 4-[(phenylcarbonyl)amino]benzene-1,3-dicarboxylic acid [CAS 121732-46-5; C. K. Lee and Y. M. Ahn, *Journal of Organic Chemistry,* 1989, 54(15), 3744-7] by treatment with thionyl chloride in an inert solvent such as 1,2-dichloromethane, by heating at reflux. The indolizine of formula (II), with $R_2$ as defined previously, reacts with the acid chloride of formula (I) in an inert solvent, such as DCM or THF, optionally in the presence of a weak base, such as triethylamine, from 0° C. to ambient temperature, to give the compound of formula (III). The regioselective introduction of a halogen atom (denoted X) in position 1 of the indolizine of formula (III) is carried out via an aromatic electrophilic substitution reaction with reactants such as, for example, iodine, NIS, NBS or bromine, optionally in the presence of a weak base such as $NaHCO_3$ in an inert solvent such as anhydrous or aqueous MeOH, dioxane or DCM, at ambient temperature, to give the halogenated derivative of formula (IV). Hydrolysis of the compound of formula (IV) in a basic aqueous medium with, for example, sodium hydroxide or potassium hydroxide, optionally in the presence of a cosolvent, such as NMP, and by heating at reflux, gives the anthranilic acid of formula (V).

The carboxylic acid of formula (V) can be activated using a reactant, such as BOP or PyBOP, in the presence of a weak base, such as, for example, triethylamine from 0° C. to ambient temperature in an inert solvent, such as DMF or THF, then reacted with glycine protected in ester form with a group $PG_1$ chosen from an alkyl group such as a methyl group or a tert-butyl group and a benzyl group, to give the compound of formula (VI). Reacting ethyl chloroformate with the compound of formula (VI) in the presence of a weak base, such as triethylamine, gives a carbamate intermediate which, after the addition of a base, such as DBU or DABCO, gives the quinazolinedione of formula (VII).

The halogenated derivative of formula (VII) can be used in an organometallic coupling reaction catalysed with palladium using, for example, $PdCl_2(dppf)$ with either aryl boronic acids or esters in the presence of a weak base, such as, for example, potassium phosphate in an inert solvent, such as DMF, while heating at 60-120° C., to give the compound of formula (VIII) comprising a group W representing a hydroxyl or else an optionally protected carboxy group, with $PG_2$ being an alkyl group chosen from a tert-butyl group and a benzyl group, or else an optionally protected group $—O(CH_2)_m$-carboxy with m and $PG_2$ as previously defined.

When the compound of formula (VIII) comprises a carboxy group protected with $PG_2$, it is treated either in an acidic medium with, for example, TFA under dry conditions at ambient temperature, or by hydrogenolysis in the presence of Pd/C in such a way as to preserve the $PG_1$ group, to give the carboxylic acid of formula (VIII).

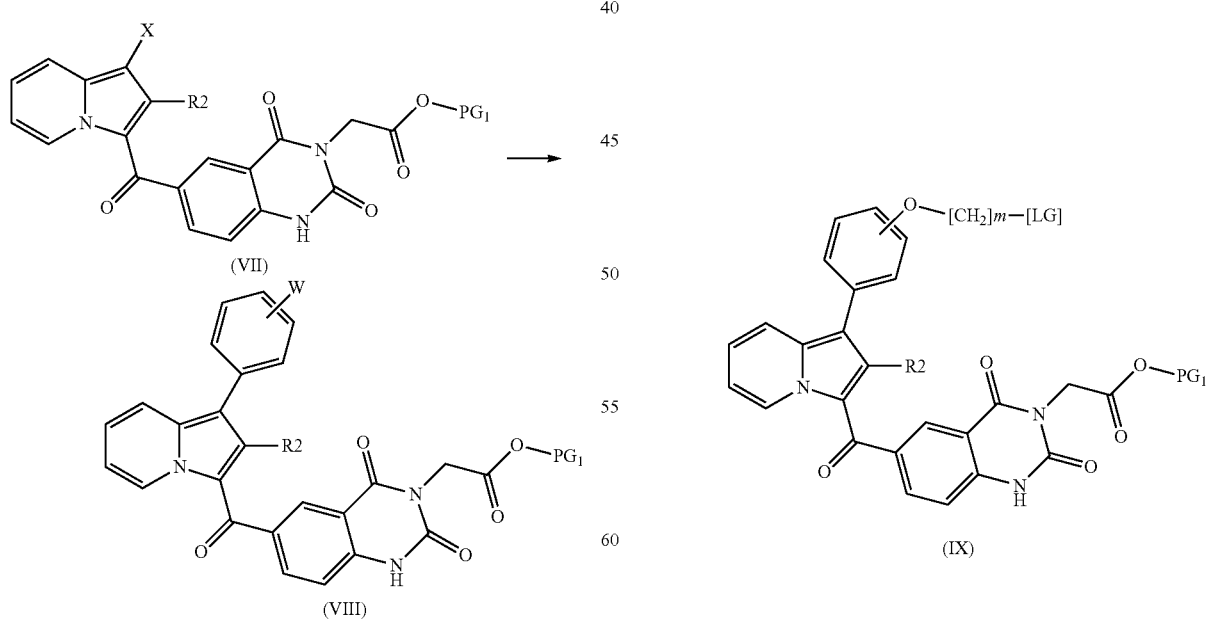

The compound of formula (VIII) when W is a hydroxyl group can react with an electrophile of formula (LG)-$(CH_2)_m$-(LG'), with m defined previously and also LG and LG', which may be identical or different, representing a halogen atom or an activated hydroxyl group, such as a mesyl, tosyl, triflate or acetyl group, after deprotonation with a base, such as, for example, sodium hydride, in an inert solvent, such as DMF or THF, at ambient temperature, to give the compound of formula (IX).

Scheme 4:

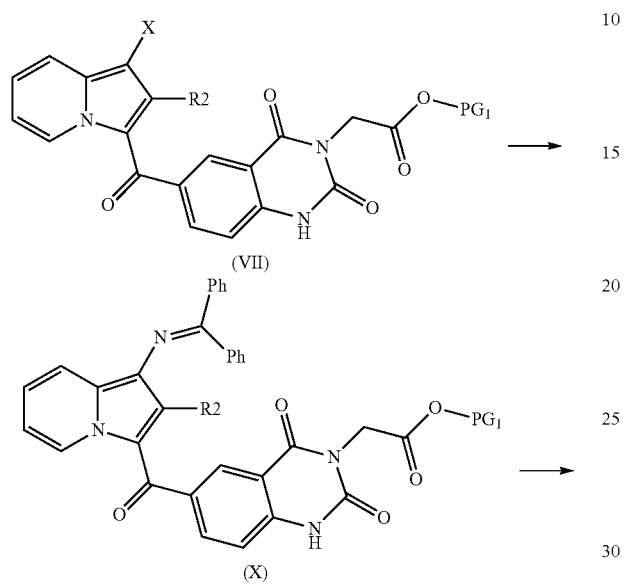

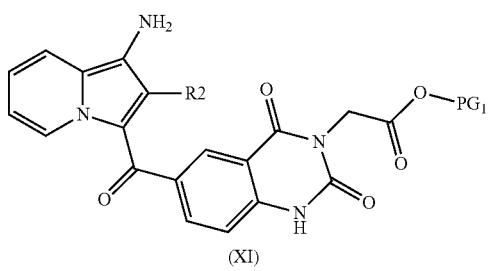

The halogenated compound of formula (VII) can be used in a coupling reaction with benzophenoneimine. This coupling is catalysed with palladium using, for example, Pd(OAc)$_2$, optionally in the presence of a ligand, such as, for example, Xantphos, in the presence of a base, such as caesium carbonate, while heating at 60-120° C. to give the imine of formula (X) which, after treatment in an acidic medium with, for example, hydrochloric acid, gives the amine of formula (XI) at ambient temperature.

Preparation of the Dimers

Scheme 5: Pathway A (Example 1)

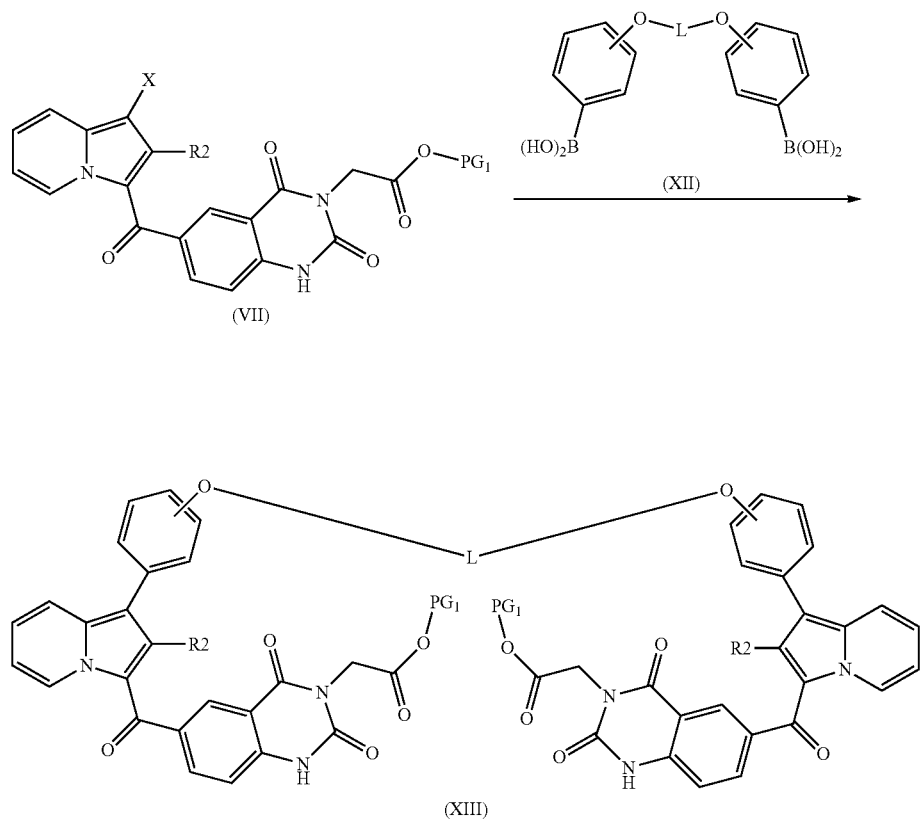

The halogenated derivative of formula (VII) can be used in an organometallic coupling reaction catalysed with palladium using, for example, PdCl$_2$(dppf) with aryl boronic acids of formula (XII) when L represents the linker A as described in application WO2007080325, in the presence of a weak base such as, for example, potassium phosphate in a solvent, such as DMF, while heating at 60-120° C., to give the compound of formula (XIII). Saponification of the esters of formula (XIII) gives the compounds of the invention.

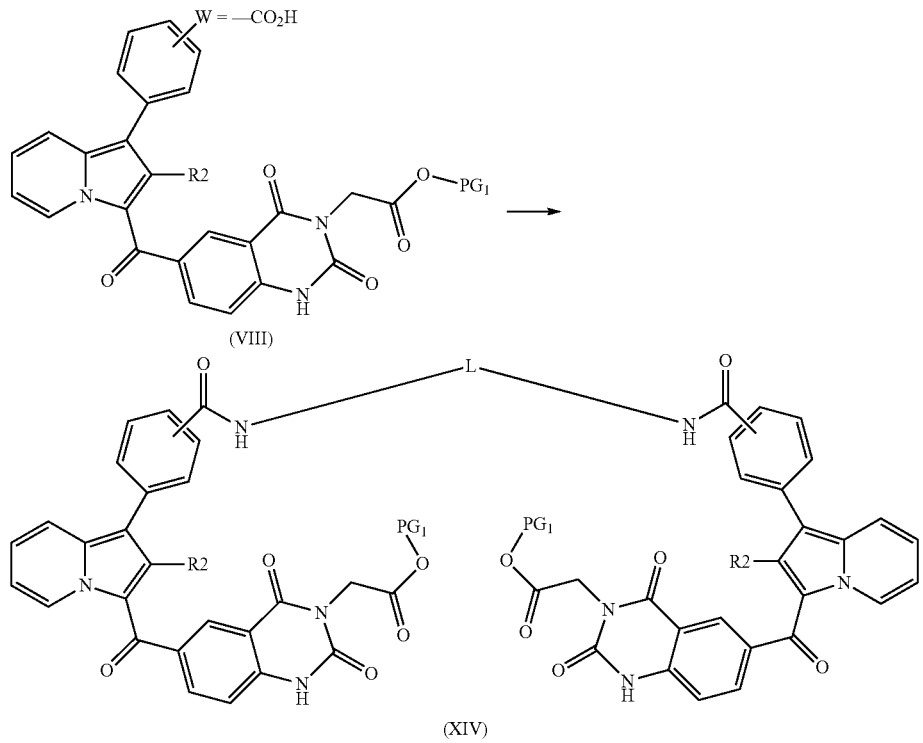

When the compound of formula (VIII) has an unprotected carboxy group W, it can be coupled to a diamine of formula H$_2$N-L-NH$_2$ after activation with, for example, BOP or PyBOP in the presence of a weak base, such as triethyl amine in a solvent such as THF or DMF, at a temperature ranging from 0° C. to ambient temperature, to give the dimers of formula (XIV). Saponification of the esters of formula (XIV) gives the compounds of the invention. The same type of reaction can be applied to the compounds of formula (VIII) when W=—O(CH$_2$)$_m$CO$_2$H.

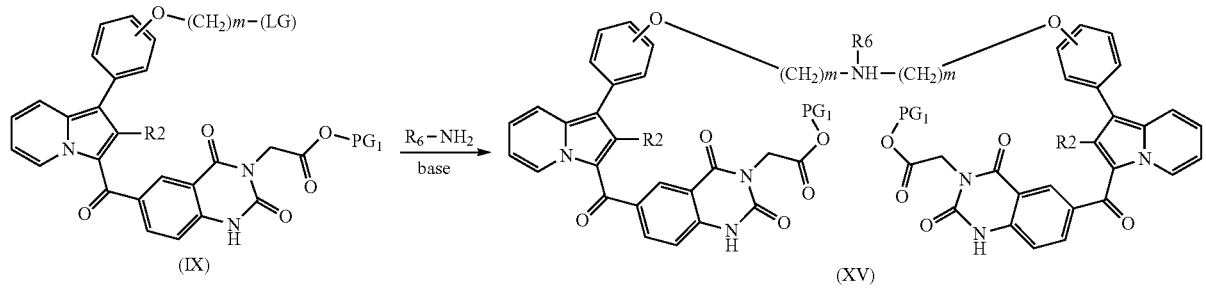

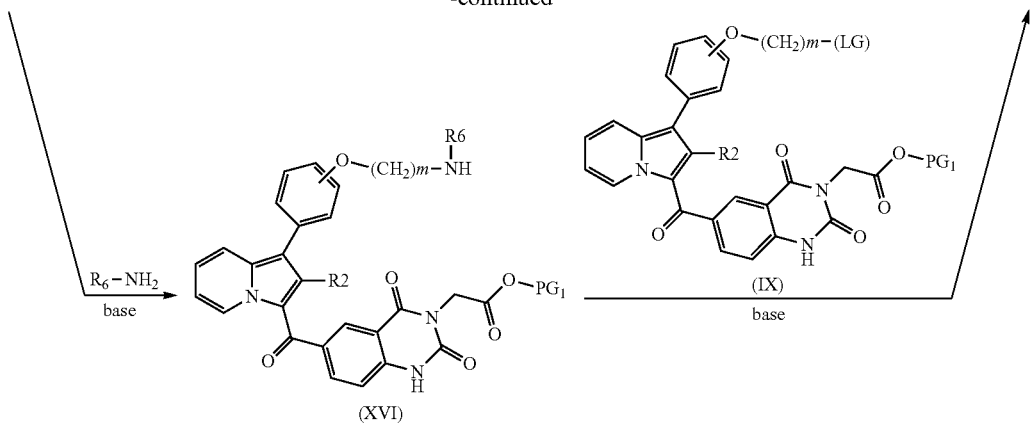

The compound of formula (IX) can be used in a nucleophilic substitution reaction with a primary amine $R_6$—$NH_2$ in the presence of a weak base, such as potassium carbonate, at ambient temperature, to give the dimer of formula (XV) or else the secondary amine of formula (XVI) when the amine $R_6$—$NH_2$ is present in great excess. The isolated amine (XVI) can react with a stoichiometric amount of the compound of formula (IX) in the presence of a weak base, such as, for example, potassium carbonate, at ambient temperature, to give the dimer of formula (XV). Saponification of the esters of formula (XV) gives the compounds of the invention.

Scheme 8: Pathway D (Example 5)

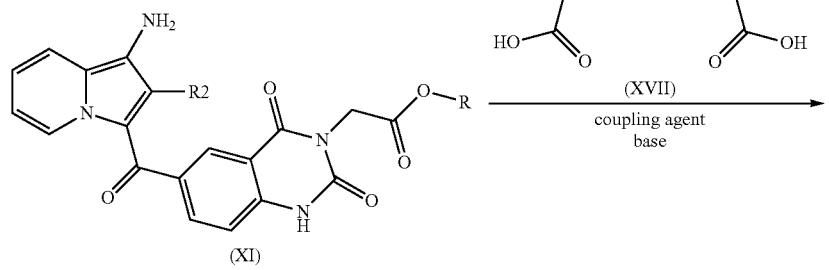

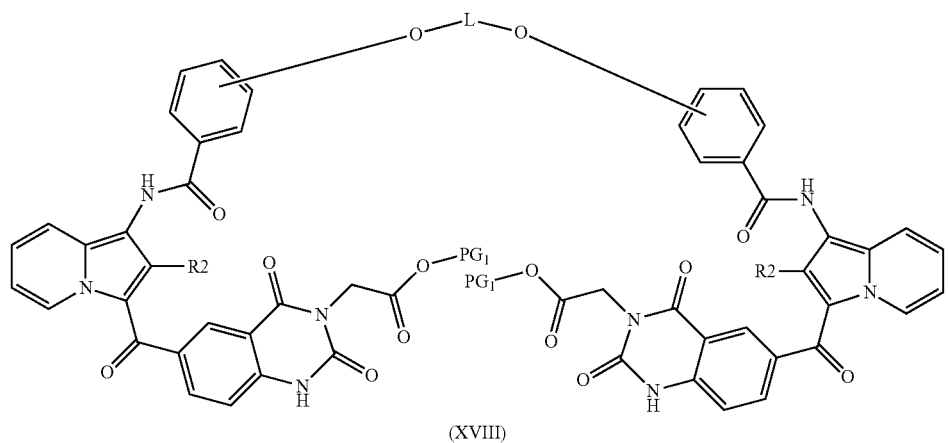

The amine of formula (XI) can be coupled to a dicarboxylic acid of formula (XVII) activated with, for example, BOP or PyBOP in the presence of a weak base, such as triethylamine, in a solvent such as THF or DMF, at a temperature ranging from 0° C. to ambient temperature, to give the dimers of formula (XVIII). Saponification of the esters of formula (XVIII) gives the compounds of the invention.

In the schemes above, the starting compounds and the reactants, when the method for preparing them is not described, are commercially available or described in the literature, or else can be prepared according to methods which are described therein or which are known to those skilled in the art.

According to another of its aspects, a subject of the invention is also the compounds of formulae (II) to (XVIII) defined above. These compounds are of use as synthesis intermediates for the compounds of formula (I).

The following examples describe the preparation of certain compounds in accordance with the invention. These examples are not limiting and merely illustrate the present invention. The numbers of the compounds exemplified refer to those given in the table hereinafter, which shows the chemical structures and the physical properties of some compounds according to the invention.

The following abbreviations and molecular formulae are used:
EtAOc=ethyl acetate
BOP=Benzotriazol-1-yloxytris(dimethylamino)phosphonium hexafluorophosphate
DABCO=1,4-diazabicyclo[2.2.2]octane
DBU=2,3,4,6,7,8,9,10-octahydropyrimido[1,2-a]azepine
DCM=dichloromethane
DMF=N,N-dimethylformamide
EtOH=ethanol
h=hour(s)
$KHSO_4$=potassium hydrogen sulphate
LCMS=Liquid Chromatography Mass Spectroscopy
MeOH=methanol
MeTHF=2-methyltetrahydrofuran
min=minute(s)
mL=milliliter(s)
(m) mol=(milli)mol(s)
$NaHCO_3$=sodium hydrogen carbonate
NBS=N-bromosuccinimide
NIS=N-iodosuccinimide
NMP=N-methyl-2-pyrrolidone
$Pd(PPh_3)_4$=tetrakis(triphenylphosphine)palladium(0)
$PdCl_2(dppf)$=1,1'-bis(diphenylphosphino)ferrocene dichloropalladium(II)
ppm=parts per million
PyBop=benzotriazol-1-yloxytrispyrrolidinophosphonium hexafluorophosphate
NMR=nuclear magnetic resonance
HBTU=2-(1H-benzotriazol-1-yl)-1,1,3,3-tetramethyluronium hexafluorophosphate
TFA=trifluoroacetic acid
THF=tetrahydrofuran
Xantphos=4,5-bis(diphenylphosphino)-9,9-dimethylxanthene In what follows:
proton magnetic resonance ($^1H$ NMR) spectra, as described below, are recorded at 400 MHz or 500 MHz in DMSO-$d_6$, using the DMSO-$d_6$ peak as a reference. The chemical shifts δ are expressed in parts per million (ppm). The signals observed are expressed in the following way: s=singlet; d=doublet; t=triplet; m=unresolved peak or br.s.=broad singlet.

EXAMPLE 1

Lysine salt of 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid (Compound No. 1)

Step 1.1. (2E)-2-[(E)-(4-methylidene-6-oxo-2-phenyl-4H-1,3-oxazin-5(6H)-ylidene)methyl]but-2-enoyl chloride Thionyl chloride (16.9 mL, 231 mmol) and 0.5 mL of DMF are added to a suspension of 4-[(phenylcarbonyl)amino]benzene-1,3-dicarboxylic acid [CAS 121732-46-5; C. K. Lee and Y. M. Ahn, *Journal of Organic Chemistry*, 1989, 54(15), 3744-7] (24.7 g, 92.61 mmol) in 310 mL of 1,2-dichloroethane. The mixture is heated at reflux for 4 h and then concentrated to dryness. The residue obtained is dissolved in toluene and then concentrated to dryness (3 times). The white solid is taken up in diisopropyl ether, filtered and dried under vacuum to give 26 g (98%) of a white powder.
$^1H$ NMR [$(CD_3)_2SO$, 250 MHz]: δ ppm 13.13 (br. s, 1H) 8.63 (d, 1H) 8.41 (dd, 1H) 8.21-8.29 (m, 2H) 7.82 (d, 1H) 7.58-7.77 (m, 3H)

Step 1.2 (5E)-4-methylidene-5-{(2E)-2-[(2-methylindolizin-3-yl)carbonyl]but-2-en-1-ylidene}-2-phenyl-4,5-dihydro-6H-1,3-oxazin-6-one A solution of 2-methylindolizine (11.5 g; 87.7 mmol) in 35 mL of THF is added dropwise to a suspension of (2E)-2-[(E)-(4-methylidene-6-oxo-2-phenyl-4H-1,3-oxazin-5(6H)-ylidene)methyl]but-2-enoyl chloride (25 g; 87.7 mmol) in 140 mL of THF at 0° C. under nitrogen. After 18 h of stirring at ambient temperature, the reaction medium is diluted in ethyl acetate, and the solution is washed with a saturated aqueous solution of sodium hydrogen carbonate, dried over sodium sulphate and concentrated to dryness. The residue obtained is purified by flash chromatography on silica (DCM) to give 22.75 g (69%) of a yellow powder.
$[M+H]^+=381$ Step 1.3 (5E)-5-{(2E)-2-[(1-bromo-2-methylindolizin-3-yl)carbonyl]but-2-en-1-ylidene}-4-methylidene-2-phenyl-4,5-dihydro-6H-1,3-oxazin-6-one N-Bromosuccinimide (10.64 g; 59.8 mmol) is added portionwise to a solution of (5E)-4-methylidene-5-{(2E)-2-[(2-methylindolizin-3-yl)carbonyl]but-2-en-1-ylidene}-2-phenyl-4,5-dihydro-6H-1,3-oxazin-6-one (22.8 g; 59.8 mmol) in 350 mL of DCM and 105 mL of NMP. After 10 min of stirring at ambient temperature, the yellow precipitate formed is filtered off, washed with DCM and dried under vacuum to give 23.2 g (85%) of the yellow powder.
$[M+H]^+=460$ Step 1.4 2-amino-5-[(1-bromo-2-methylindolizin-3-yl)carbonyl]benzoic acid The (5E)-5-{(2E)-2-[(1-bromo-2-methylindolizin-3-yl)carbonyl]but-2-en-1-ylidene}-4-methylidene-2-phenyl-4,5-dihydro-6H-1,3-oxazin-6-one (18.6 g; 40.4 mmol) is added portionwise to potassium hydroxide (22.7 g; 0.40 mol) in 100 mL of water and 140 mL of NMP. The reaction mixture is heated at reflux for 18 h, cooled to ambient temperature and poured into a hydrochloric acid solution (1 M). The yellow precipitate formed is filtered off and dried under vacuum to give 16.5 g (99%) of a yellow powder.

[M+H]$^+$=374

Step 1.5 methyl N-({2-amino-5-[(1-bromo-2-methylindolizin-3-yl)carbonyl]phenyl}carbonyl)glycinate Triethylamine (7.34 mL; 52.3 mmol) and PyBOP (9.97 g; 19.2 mmol) are added to a solution of 2-amino-5-[(1-bromo-2-methylindolizin-3-yl)carbonyl]benzoic acid (6.5 g; 17.4 mmol) in 58 mL of NMP at 0° C. under nitrogen. After 30 min of stirring at 0° C., glycine methyl ester hydrochloride (2.4 g; 19.2 mmol) is added. After 1 h of stirring at ambient temperature, the reaction medium is run into a saturated aqueous solution of sodium hydrogen carbonate. The yellow precipitate formed is filtered off and dried under vacuum to give 6.45 g (83%) of a yellow powder.

[M+H]$^+$=444

Step 1.6 methyl {6-[(1-bromo-2-methylindolizin-3-yl)carbonyl]-2,4-dioxo-1,4-dihydroquinazolin-3 (2H)-yl}acetate Ethyl chloroformate (1.3 mL; 13.5 mmol) is added dropwise to a solution of methyl N-({2-amino-5-[(1-bromo-2-methylindolizin-3-yl)carbonyl]phenyl}carbonyl)glycinate (2 g; 4.5 mmol) in 9 mL of pyridine at 0° C. After 15 min of stirring at ambient temperature, the reaction medium is concentrated to dryness and then diluted with ethyl acetate. The solution is washed with a 0.1 M hydrochloric acid solution and a saturated solution of sodium chloride, dried over sodium sulphate and concentrated to dryness. The yellow solid obtained is dissolved in 20 mL of anhydrous tetrahydrofuran and heated at reflux in the presence of diaza(1,3) bicyclo[5,4,0]undec-7-ene (1.35 mL; 9 mmol) for 1 h. The reaction medium is diluted with ethyl acetate, washed with a 0.1 M hydrochloric acid solution and a saturated solution of sodium chloride, dried over sodium sulphate and concentrated to dryness to give 2 g (95%) of a yellow powder.

[M+H]$^+$=470

Step 1.7 methyl 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetate Methyl {6-[(1-bromo-2-methylindolizin-3-yl)carbonyl]-2,4-dioxo-1,4-dihydroquinazolin-3(2H)-yl}acetate (0.34 g; 0.74 mmol; 2 eq), [oxybis(ethane-2,1-diyloxyethane-2,1-diyloxybenzene-4,1-diyl)]diboronic acid [CAS 944446-98-4; WO 2007080325 A1] (0.16 g; 0.37 mmol), a molar solution of tribasic potassium phosphate (2.2 mL; 2.21 mmol), 9 mL of DMF and the catalyst PdCl$_2$(dppf) (0.08 g; 0.11 mmol) are successively introduced into a reactor under argon. The reaction mixture is heated at 90° C. for 24 h, cooled to ambient temperature and concentrated to dryness. The residue obtained is purified by preparative HPLC on Kromasil C18 reverse phase [A=H$_2$O/(CH$_3$COONH$_4$ 0.1 M) 90/10; B=CH$_3$CN/(CH$_3$COONH$_4$ 0.1 M) 90/10, gradient A/B: 90/10 to 22/78] to give 84 mg (20%) of a yellow powder.

[M−H]$^-$=1125

Step 1.8 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid A molar solution of sodium hydroxide (0.15 mL; 0.15 mmol) is added to a solution of methyl 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetate (107 mg; 0.10 mmol) in 4 mL of NMP. The solution is stirred at ambient temperature for 24 h and then run into a hydrochloric acid solution (0.1 M). The precipitate obtained is filtered off, washed with water and dried under vacuum to give 101 mg (97%) of a yellow-orange powder.

[M−H]$^-$=1095

Step 1.9 lysine salt of 2,2'-{oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid 2,2'-{Oxybis[ethane-2,1-diyloxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid (101 mg; 0.09 mmol) is added to a solution of lysine (27 mg; 0.14 mmol) in 3 mL of water. The solution is stirred for 4 h, filtered and lyophilized. The lyophilisate is taken up in diethyl ether and the suspension is stirred for 3 h, filtered and dried under vacuum to give 112 mg (2 lysine; 87%) of a yellow powder.

LCMS (method 1): [M−H]$^-$=1095, RT=7.21 min $^1$H NMR [(CD$_3$)$_2$SO, 400 MHz]: δ ppm 9.42 (d, 2H) 8.09 (d, 2H) 7.87 (dd, 2H) 7.43 (d, 2H) 7.30 (d, 2H) 7.23 (d, 4H) 7.14 (td, 2H) 7.01 (d, 4H) 6.91 (td, 2H) 6.50-9.00 (br. s, 8H) 4.28 (s, 4H) 4.11 (m, 4H) 3.78 (m, 4H) 3.55-3.64 (m, 8H) 3.15 (t, 2H) 2.72 (t, 4H) 1.77 (s, 6H) 1.28-1.73 (m, 12H)

EXAMPLE 2

2,2'-{hexane-1,6-diylbis[imino(2-oxoethane-2,1-diyl)oxybenzene-4,1-diyl(2-methylindolizine-1,3-diyl)carbonyl(2,4-dioxo-1,4-dihydroquinazoline-6,3(2H)-diyl)]}diacetic acid (Compound No. 4)

Step 2.1 methyl[6-({1-[4-(2-tert-butoxy-2-oxoethoxy)phenyl]-2-methylindolizin-3-yl}carbonyl)-2,4-dioxo-1,4-dihydroquinazolin-3(2H)-yl]acetate Methyl {6-[(1-bromo-2-methylindolizin-3-yl)carbonyl]-2,4-dioxo-1,4-dihydroquinazolin-3(2H)-yl}acetate [described in Step 1.5.] (0.85 g; 1.81 mmol), tert-butyl[4-(4,4,5,5-tetramethyl-1,3,2-dioxaborolan-2yl)phenoxy]acetate [CAS 769968-17-4; D. Fan et al, Journal of Organic Chemistry, 2007, 72(14), 5350-5357] (0.91 g; 2.71 mmol), 5.4 mL of a molar solution of potassium phosphate, 17 mL of 1,2-dimethoxyethane and the catalyst PdCl$_2$(dppf) (198 mg; 0.27 mmol) are successively introduced into a reactor, under argon. The mixture is heated at reflux for 2 hours under argon. The reaction medium is filtered through Celite. The filtrate is diluted with ethyl acetate and the solution is washed with a saturated solution of potassium hydrogen carbonate and with a saturated solution of sodium chloride, and then dried over sodium sulphate and concentrated to dryness. The residue obtained is purified by flash chromatography on silica (DCM/EtOH: 100/0 to 80/10). 0.46 g (42%) of a yellow-red powder is obtained.

[M+H]$^+$=598

Step 2.2 [4-(3-{[3-(2-methoxy-2-oxoethyl)-2,4-dioxo-1,2,3,4-tetrahydroquinazolin-6-yl]carbonyl}-2-methylindolizin-1-yl)phenoxy]acetic acid Trifluoroacetic acid (1.2 mL; 15.4 mmol) is added to a solution of methyl 6-({1-[4-(2-tert-butoxy-2-oxoethoxy)

phenyl]-2-methylindolizin-3-yl}carbonyl)-2,4-dioxo-1,4-dihydroquinazolin-3(2H)-yl]acetate (0.46 g; 0.77 mmol) in 4 mL of dichloromethane. The solution is stirred at ambient temperature for 4 h and then concentrated to dryness. The residue obtained is taken up in 5 mL of N,N-dimethylformamide and run into a saturated aqueous solution of sodium hydrogen carbonate. The solution is washed with a THF/EtOAc mixture, then neutralized to pH 7 by adding a molar solution of hydrochloric acid. The precipitate formed is filtered off and dried under vacuum to give 0.36 g (87%) of a yellow powder.

[M+H]$^+$=542

Step 2.3 methyl 2,2'-{hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetate Triethylamine (100 µl; 0.68 mmol), PyBOP (221 mg; 0.43 mmol) and hexane-1,6-diamine (20 µl; 0.17 mmo) are successively added to a solution of [4-(3-{[3-(2-methoxy-2-oxoethyl)-2,4-dioxo-1,2,3,4-tetrahydroquinazolin-6-yl]carbonyl}-2-methylindolizin-1-yl)phenoxy]acetic acid (184 mg; 0.34 mmol) in 3 mL of NMP at 0° C. under nitrogen. The reaction mixture is stirred at ambient temperature for 17 h and then poured into an ethyl acetate/THF mixture. The organic solution is washed with a 0.1 M hydrochloric acid solution, with a saturated solution of sodium hydrogen carbonate and with a saturated solution of sodium chloride, and then dried over sodium sulphate and concentrated to dryness to give a brown paste which is used in the following saponification step.

[M+H]$^+$=165

Step 2.4 2,2'-{hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid Obtained according to the process described in Step 1.8, using methyl 2,2'-{hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetate, in the form of a yellow powder (32% for the 2 steps).

[M−H]$^-$=1133

Step 2.5 sodium salt of 2,2'-{hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid 2,2'-{Hexane-1,6-diylbis[imino(2-oxoethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid is added to a solution of sodium hydroxide (1 M, 70 µl; 0.07 mmol) diluted in 20 mL of water. The solution is stirred at ambient temperature and then lyophilized. The lyophilisate is taken up in diisopropyl ether, filtered and dried under vacuum to give 29 mg (sodium salt; 84%) of a yellow powder.

LCMS (method 1): [M−H]$^-$=1133; RT=6.90 min $^1$H NMR [(CD$_3$)$_2$SO, 400 MHz]: δ ppm 9.45 (d, 2H) 8.15 (d, 2H) 8.12 (t, 2H) 7.91 (dd, 2H) 7.48 (d, 2H) 7.32 (d, 6H) 7.21 (td, 2H) 7.05 (d, 4H) 6.96 (td, 2H) 4.49 (s, 4H) 4.21 (s, 4H) 3.06-3.16 (m, 6H) 2.62-2.70 (m, 4H) 1.84 (s, 6H) 1.17-1.76 (m, 20H)

EXAMPLE 3

Sodium salt of 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid (Compound No. 8)

Step 3.1 tert-butyl N-({2-amino-5-[(1-bromo-2-methylindolizin-3-yl)carbonyl]phenyl}carbonyl)glycinate Obtained according to the process described in Step 1.5, using 2-amino-5-[(1-bromo-2-methylindolizin-3-yl)carbonyl]benzoic acid and the tert-butyl ester of glycine, in the form of a yellow powder (74%).

[M+H]$^+$=486.0

Step 3.2 tert-butyl {7-[(1-bromo-2-methylindolizin-3-yl)carbonyl]-2,4-dioxo-1,4-dihydroquinazolin-3(2H)-yl}acetate Obtained according to the process described in Step 1.6, using tert-butyl N-({2-amino-5-[(1-bromo-2-methylindolizin-3-yl)carbonyl]phenyl}carbonyl)glycinate, in the form of a yellow powder (52%).

[M+H]$^+$=511.9

Step 3.3 tert-butyl[7-{([1-(4-hydroxyphenyl)-2-methylindolizin-3-yl]carbonyl}-2,4-dioxo-1,4-dihydroquinazolin-3(2H)-yl]acetate (4-Hydroxyphenyl)boronic acid (404 mg, 2.93 mmol), 3 mL of a 2 M potassium phosphate solution (5.86 mmol) and the catalyst PdCl$_2$(dppf) (206 mg, 0.29 mmol) are added to a solution of tert-butyl {7-[(1-bromo-2-methylindolizin-3-yl)carbonyl]-2,4-dioxo-1,4-dihydroquinazolin-3(2H)-yl}acetate (1 g, 1.95 mmol) in 20 mL of DMF, placed in a microwave reactor under nitrogen. The reactor is sealed and the solution is heated for 30 min at 120° C. in a microwave. The reaction medium is run into water and extracted with EtOAc. The organic phase is washed with a saturated aqueous solution of NaCl, dried over Na$_2$SO$_4$, and concentrated to dryness. The oil obtained is purified by flash chromatography on silica (DCM/EtOH: 100/0 to 90/10] to give 888 mg (86%) of a yellow solid.

[M+H]$^+$=526.0

Step 3.4 tert-butyl {7-[(1-{(4-[(5-chloropentyl)oxy]phenyl}-2-methylindolizin-3-yl)carbonyl]-2,4-dioxo-1,4-dihydroquinazolin-3(2H)-yl}acetate Sodium hydride (suspension in 60% oil, 332 mg, 7.61 mmol) is added to a solution of tert-butyl[7-{[1-(4-hydroxyphenyl)-2-methylindolizin-3-yl]carbonyl}-2,4-dioxo-1,4-dihydroquinazolin-3(2H)-yl]acetate (2 g, 3.81 mmol) in solution in 38 mL of DMF at −5° C. After 15 min of stirring at −5° C., 1-chloro-5-iodopentane (0.53 mL, 3.81 mmol) is added. The reaction mixture is stirred for 3 h at −5° C., cooled to ambient temperature and run into a molar solution of KHSO$_4$. The yellow precipitate obtained is filtered off and then purified by flash chromatography on silica (DCM/EtOH: 100/0 to 90/10) to give 2.11 g (yield: 88%) of a yellow solid.

[M+H]$^+$=629.2

Step 3.5 tert-butyl {7-[(1-{(4-[(5-iodopentyl)oxy]phenyl}-2-methylindolizin-3-yl)carbonyl]-2,4-dioxo-1,4-dihydroquinazolin-3(2H)-yl}acetate A mixture of tert-butyl {7-[(1-{4-[(5-chloropentyl)oxy]phenyl}-2-methylindolizin-3-yl)carbonyl]-2,4-dioxo-1,4-dihydroquinazolin-3(2H)-yl}acetate (4.0 g, 6.35 mmol) and potassium iodide (10.53 g, 63.48 mmol) in 63 mL of DMF is stirred at 80° C. for 6 h. It is cooled to ambient temperature and run into a molar solution of $KHSO_4$. The yellow precipitate obtained is filtered off and then washed with water and dried under vacuum to give 3.96 g (yield: 86%) of a yellow solid.
$[M+H]^+=722.3$ Step 3.6 tert-butyl {7-[(1-{4-[(5-{[2-(2-hydroxyethoxy)ethyl]amino}pentyl)oxy]phenyl}-2-methylindolizin-3-yl)carbonyl]-2,4-dioxo-1,4-dihydroquinazolin-3(2H)-yl}acetate Potassium carbonate (0.48 g, 3.46 mmol) and tert-butyl {7-[(1-{4-[(5-iodopentyl)oxy]phenyl}-2-methylindolizin-3-yl)carbonyl]-2,4-dioxo-1,4-dihydroquinazolin-3(2H)-yl}acetate (0.50 g, 0.69 mmol) are added to a solution of 2-(2-aminoethoxy)ethanol (0.73 g, 6.93 mmol) in 7 mL of DMF. The solution is stirred for 24 h at ambient temperature and then run into a molar solution of $KHSO_4$. The precipitate formed is filtered off, washed with water and dried under vacuum to give 380 mg (yield: 79%) of a brown powder.
$[M+H]^+=699.3$ Step 3.7 tert-butyl 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetate tert-Butyl {7-[(1-{4-[(5-iodopentyl)oxy]phenyl}-2-methylindolizin-3-yl)carbonyl]-2,4-dioxo-1,4-dihydroquinazolin-3(2H)-yl}acetate (0.54 g, 0.75 mmol) is added to a mixture of tert-butyl {7-[(1-{4-[(5-{[2-(2-hydroxyethoxy)ethyl]amino}pentyl)oxy]phenyl}-2-methylindolizin-3-yl)carbonyl]-2,4-dioxo-1,4-dihydroquinazolin-3(2H)-yl}acetate (0.35 g, 0.50 mmol) and potassium carbonate (104 mg, 0.75 mmol) in 5 mL of DMF. The reaction mixture is stirred for 24 h at ambient temperature and then run into a molar solution of $KHSO_4$. The precipitate formed is filtered off, washed with water and dried under vacuum to give 588 mg (yield: 90%) of a brown powder.
$[M+H]^+=1291.4$ Step 3.8 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid Trifluoroacetic acid (0.44 g, 3.89 mmol) is added to the tert-butyl 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetate (0.50 g, 0.39 mmol) in suspension in 4 mL of a DCM/MeOH mixture (1/1). The solution is stirred for 8 h at ambient temperature. The reaction mixture is run into water. The precipitate formed is filtered off, washed with water then with ethanol, and dried under vacuum. Purification by preparative HPLC on Kromasil C18 10 μm reverse phase [A=$H_2O$/($CH_3COONH_4$ 0.1 M) 90/10; B=$CH_3CN$/($CH_3COONH_4$ 0.1 M) 90/10, gradient A/B: 70/30 to 56/44] gives 25 mg (5%) of a yellow powder.
$[M+H]^+=1180.2$ Step 3.9 sodium salt of 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid Obtained according to the process described in Step 2.5, using 2,2'-({[2-(2-hydroxyethoxy)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)]) diacetic acid (25 mg, 0.02 mmol), in the form of a yellow solid.
LCMS (method 1): $[M+H]^+=1180$, RT=7.36 min
$^1$H NMR [($CD_3$)$_2$SO, 500 MHz]: δ ppm 9.20 (br. s., 2H) 8.09 (d, 2H) 7.69 (br. s., 2H) 7.44 (d, 2H) 7.31 (d, 4H) 7.04-7.11 (td, 2H) 7.02 (d, 4H) 6.85 (td, 2H) 4.65 (br. s., 1H) 4.13 (s, 4H) 4.00 (t, 4H) 3.46 (t, 4H) 3.40 (t, 2H) 2.56 (t, 2H) 2.43 (t, 4H) 1.94 (s, 6H) 1.75 (m, 4H) 1.39-1.50 (m, 8H)

EXAMPLE 4

[7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]acetic acid
(Compound No. 16)

Step 4.1. benzyl 4-(3-{[3-(2-tert-butoxy-2-oxoethyl)-2,4-dioxo-1,2,3,4-tetrahydroquinazolin-7-yl]carbonyl}-2-methylindolizin-1-yl)benzoate {4-[(Benzyloxy)carbonyl]phenyl}boronic acid (0.7 g, 2.73 mmol), 5.5 mL of a molar solution of potassium phosphate and the catalyst $PdCl_2$(dppf) (192 mg, 0.27 mmol) are added to a solution of tert-butyl {7-[(1-bromo-2-methylindolizin-3-yl)carbonyl]-2,4-dioxo-1,4-dihydroquinazolin-3(2H)-yl}acetate [described in Step 3.2.] (1 g, 1.82 mmol) in 20 mL of DMF placed in a microwave reactor under nitrogen. The reactor is sealed and the solution is heated for 30 min at 80° C. in a microwave. The reaction medium is cooled and run into a molar solution of $KHSO_4$, and extracted with EtOAc. The organic phase is washed with a saturated aqueous solution of NaCl, dried over $Na_2SO_4$, and concentrated to dryness. The residue obtained is purified by flash chromatography on silica (DCM/EtOH: 100/0 to 80/20) to give 1.08 mg (92%) of a yellow solid.
$[M+H]^+=644.2$ Step 4.2. 4-(3-{[3-(2-tert-butoxy-2-oxoethyl)-2,4-dioxo-1,2,3,4-tetrahydroquinazolin-7-yl]carbonyl}-2-methylindolizin-1-yl)benzoic acid Palladium on carbon (10% active, 0.2 g) and benzyl 4-(3-{[3-(2-tert-butoxy-2-oxoethyl)-2,4-dioxo-1,2,3,4-tetrahydroquinazolin-7-yl]carbonyl}-2-methylindolizin-1-yl)benzoate (1 g, 1.55 mmol) are added, under nitrogen, to ammonium formate (0.97 g, 15.54 mmol) in solution in 15 mL of DMF. The reaction mixture is stirred for 3 h at ambient temperature and filtered through Celite, and the filtrate is concentrated to dryness. The solid obtained is taken up in diisopropyl ether. After filtration and drying under vacuum, 732 mg (yield: 85%) of a green solid are obtained.
[M+H]$^+$=554.1

Step 4.3. tert-butyl[7-({1-[4-({9-[4-(3-{[3-(2-tert-butoxy-2-oxoethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]acetate Triethylamine (0.25 mL, 1.81 mmol) and HBTU (0.16 g, 0.40 mmol) are added to a solution of 4-(3-{[3-(2-tert-butoxy-2-oxoethyl)-2,4-dioxo-1,2,3,4-tetrahydroquinazolin-7-yl]carbonyl}-2-methylindolizin-1-yl)benzoic acid (0.2 g, 0.36 mmol) in 10 mL of DMF at 0° C. After stirring for 15 min, bis(2-aminoethanol) hydrogen phosphate (0.046 g, 0.18 mmol) is added. The reaction mixture is stirred for 24 h at ambient temperature and then run into water. The precipitate formed is filtered off and dried under vacuum to give 156 mg (yield: 34%) of a yellow solid.
[M+H]$^+$=1255.2

Step 4.4. [7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]acetic acid Obtained according to the process described in Step 3.7, using tert-butyl 7-({1-[4-({9-[4-(3-{[3-(2-tert-butoxy-2-oxoethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]acetate, and after purification by preparative HPLC on Kromasil C18 10 µm reverse phase [A=H$_2$O/(CH$_3$COONH$_4$ 0.1 M) 90/10; B=CH$_3$CN/(CH$_3$COONH$_4$ 0.1 M) 90/10, gradient NB 95/5 to 70/30], in the form of a yellow powder (yield=3%).
[M+H]$^+$=1143.2

Step 4.5. sodium salt of [7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]acetic acid Obtained according to the process described in step 2.5, using [7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphanon-1-yl}carbamoyl)phenyl]-2-methylindolizin-3-yl}carbonyl)-2,4-dioxo-1,4-dihydroquinazolin-3(2H)-yl]diacetic acid, in the form of a yellow solid (yield: 75%).
LCMS (method 2): [M+H]$^+$=1143, RT=9.98 min
$^1$H NMR [(CD$_3$)$_2$SO, 500 MHz]: δ ppm 11.87 (br. s., 2H) 9.77 (t, 2H) 9.41 (d, 2H) 8.15 (d, 2H) 8.04 (d, 4H) 7.89 (dd, 2H) 7.52 (d, 2H) 7.42 (d, 4H) 7.32 (d, 2H) 7.20 (td, 2H) 6.97 (td, 2H) 4.24 (s, 4H) 3.89-3.96 (m, 4H) 3.42 (q, 4H) 1.84 (s, 6H)

EXAMPLE 5

Sodium salt of 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetic acid (Compound No. 21)

Step 5.1. tert-butyl[7-({1-[(diphenylmethylidene)amino]-2-methylindolizin-3-yl}carbonyl)-2,4-dioxo-1,4-dihydroquinazolin-3(2H)-yl]acetate Caesium carbonate (0.51 g, 1.59 mmol), Xantphos (0.98 g, 1.70 mmol), palladium acetate (0.19 g, 0.85 mmol) and benzophenoneimine (2.85 mL, 17.0 mmol) are added to a solution of methyl {6-[(1-bromo-2-methylindolizin-3-yl)carbonyl]-2,4-dioxo-1,4-dihydroquinazolin-3(2H)-yl}acetate [described in Step 1.5.] (2.0 g, 4.25 mmol) in 90 mL of DMF under argon. The reaction medium is stirred under argon at 100° C. for 2 days. After cooling, the reaction medium is diluted with ethyl acetate, and the solution is washed with a saturated solution of sodium chloride, dried over sodium sulphate and concentrated to dryness. The oil obtained is purified by flash chromatography on silica (toluene/EtOAc: 100/0 to 50/50] to give 1.33 g of a red powder.
[MH]$^+$=571.2

Step 5.2. methyl {7-[(1-amino-2-methylindolizin-3-yl)carbonyl]-2,4-dioxo-1,4-dihydroquinazolin-3(2H)-yl}acetate hydrochloride 0.53 mL of a 4 M solution of hydrochloric acid in anhydrous dioxane is added to a solution of tert-butyl[7-({1-[(diphenylmethylidene)amino]-2-methylindolizin-3-yl}carbonyl)-2,4-dioxo-1,4-dihydroquinazolin-3(2H)-yl]acetate (1.3 g, 1.34 mmol) in 7 mL of a DCM/MeOH mixture (5/1). After 24 h of stirring at ambient temperature, the precipitate formed is filtered off, washed with DCM and dried under vacuum at 40° C. to give 0.4 g (hydrochloride; 67%) of a yellow powder.
[MH]$^+$=407.1

Step 5.3 methyl 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetate Triethylamine (0.23 mL, 1.63 mmol) and HBTU (285 mg, 0.75 mmol) are added to a suspension of 3,3'-{ethane-1,2-diylbis[imino(2-oxoethane-2,1-diyl)oxy]}dibenzoic acid [CAS 944446-34-8; WO 2007080325] (136 mg, 0.33 mmol) in 5 mL of DMF at 0° C. After stirring for 30 min, methyl {7-[(1-amino-2-methylindolizin-3-yl)carbonyl]-2,4-dioxo-1,4-dihydroquinazolin-3(2H)-yl}acetate hydrochloride (318 mg, 0.72 mmol) is added. The solution is stirred for 10 h at ambient temperature and then run into a saturated aqueous solution of sodium hydrogen carbonate. The precipitate is filtered off and washed with water and then dried under vacuum to give 370 mg (yield: 94%) of a green solid.
[MH]$^+$=1193.3

Step 5.4 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetic acid Obtained according to the process described in Step 1.8, using methyl 2,2'-{ethane-1,2-diylbis[imino(2-oxoethane-2, 1-diyloxybenzene-3,1-diylcarbonylimino(2-methylindolizine-1,3-diyl)carbonyl(2,4-dioxo-1,4-dihydroquinazoline-7,3(2H)-diyl)]}diacetate, and after purification by preparative HPLC on Kromasil C18 10 μm reverse phase [A=H$_2$O/(CH$_3$COONH$_4$ 0.1 M) 90/10; B=CH$_3$CN/(CH$_3$COONH$_4$ 0.1 M) 90/10, gradient NB: 95/5 to 69/31], in the form of a yellow powder (yield=59%).

[MH]$^+$=1165.1

Step 5.5. sodium salt of 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetic acid Obtained according to the process described in Step 2.5, using 2,2'-{ethane-1,2-diylbis[imino(2-oxoethane-2,1-diyloxybenzene-3,1-diylcarbonylimino(2-methylindolizine-1,3-diyl)carbonyl(2,4-dioxo-1,4-dihydroquinazoline-7,3(2H)-diyl)]}diacetic acid, in the form of a yellow solid (yield: 70%).

LCMS (method 2): [M+H]$^+$=1165, RT=5.95 min $^1$H NMR [(CD$_3$)$_2$SO, 500 MHz]: δ ppm 10.23 (br. s., 2H) 9.44 (br. s, 2H) 8.44 (br. s, 2H) 8.08 (d, 2H) 7.81 (br. s., 2H) 7.64-7.70 (m, 4H) 7.47 (d, 2H) 7.42 (t, 2H) 7.20 (td, 2H) 7.17 (br. s., 2H) 7.15 (dd, 2H) 6.95 (td, 2H) 4.53 (s, 4H) 4.12 (s, 4H) 3.20-3.24 (m, 4H) 1.81 (s, 6H)

The table which follows illustrates the chemical structures and the physical properties of some examples of compounds according to the invention. In this table:

in the "salt" column, "Lys" and "Na" represent, respectively, a compound in D,L-lysine salt or sodium salt form, and the ratio between parentheses is the (base: diacid) ratio, Ph represents a phenyl group, the RT column indicates the retention time of the compound, and the LCMS characteristics, as described below, indicate successively the analytical method of high-performance liquid chromatography used and detailed below (method 1 or 2), the [M−H]$^−$ or [M+H]$^+$ peak identified by mass spectrometry and the retention time of the compound, expressed in minutes.

Method 1

Instrument: HPLC system of the 1100 (Agilent) type; simple quadrupole mass spectrometer of the MSD (Agilent) type Column: Waters X Terra C18 3.5 μm (2.1×50 mm)

Solvent A: H$_2$O+AcONH$_4$ 10 mM pH 7; Solvent B: CH$_3$CN

Flow rate: 0.4 mL/min

Gradient: t 0 min 0% of B; t 10 min 90% of B; t 15 min 90% of B

Detection: UV 220 nm

Ionization: positive electrospray mode ESI+ or ESI−

Method 2: See Method 1 with Change of Gradient

Gradient: t 0 min 0% of B; t 30 min 90% of B; t 35 min 90% of B

Table of examples
M$_1$—L—M$_2$
with M having the general formula as below:

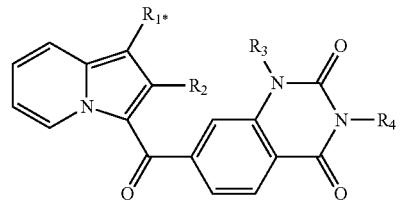

(M)

| No. | R1 | R2 | R3 | R4 | L | Salt | [M − H]$^−$ | [M + H]$^+$ | RT (min) | LCMS Method |
|---|---|---|---|---|---|---|---|---|---|---|
| 1 | —Ph-4-O* | —CH$_3$ | H | CH$_2$COOH | *(CH$_2$)$_2$[O(CH$_2$)$_2$]$_2$O(CH$_2$)$_2$* | Lys (2) | 1095 | / | 7.21 | 1 |
| 2 | —Ph-3-O* | —CH$_3$ | H | CH$_2$COOH | *(CH$_2$)$_2$[O(CH$_2$)$_2$]$_2$O(CH$_2$)$_2$* | Lys (2) | 1095 | / | 7.28 | 1 |
| 3 | —Ph-4-O* | —CH$_3$ | H | CH$_2$COOH | *(CH$_2$)$_2$O(CH$_2$)$_2$O(CH$_2$)$_2$* | Lys (3) | 1051 | / | 7.28 | 1 |
| 4 | —Ph-4-O* | —CH$_3$ | H | CH$_2$COOH | *CH$_2$CONH(CH$_2$)$_6$NHCOCH$_2$* | Lys (2) | 1133 | / | 6.90 | 1 |
| 5 | —Ph-4-O* | —CH$_3$ | H | CH$_2$COOH | *CH$_2$CONH(CH$_2$)$_4$NHCOCH$_2$* | Na (2) | 1105 | / | 6.56 | 1 |
| 6 | —Ph-3-O* | —CH$_3$ | H | CH$_2$COOH | *CH$_2$CONH(CH$_2$)$_6$NHCOCH$_2$* | Na (2) | 1133 | / | 6.91 | 1 |
| 7 | —Ph-3-O* | —CH$_3$ | H | CH$_2$COOH | *CH$_2$CONH(CH$_2$)$_4$NHCOCH$_2$* | Na (2) | 1105 | / | 6.65 | 1 |
| 8 | —Ph-4-O* | —CH$_3$ | H | CH$_2$COOH | *(CH$_2$)$_5$N[(CH$_2$)$_2$O(CH$_2$)$_2$OH](CH$_2$)$_5$* | Na (2) | / | 1180 | 7.36 | 1 |
| 9 | —Ph-4-O* | —CH$_3$ | H | CH$_2$COOH | *(CH$_2$)$_5$N[CH$_2$CH$_3$](CH$_2$)$_5$* | Na (2) | / | 1120 | 7.50 | 1 |
| 10 | —Ph-4-O* | —CH$_3$ | H | CH$_2$COOH | *(CH$_2$)$_5$N[(CH$_2$)$_2$N-morpholine](CH$_2$)$_5$* | Na (2) | / | 1205 | 15.66 | 2 |
| 11 | —Ph-4-O* | —CH$_3$ | H | CH$_2$COOH | *(CH$_2$)$_5$N[(CH$_2$)$_2$N—(N-methylpiperazine)](CH$_2$)$_5$* | Na (2) | / | 1218 | 15.41 | 2 |
| 12 | —Ph-4-O* | —CH$_3$ | H | CH$_2$COOH | *(CH$_2$)$_5$N[(CH$_2$)-pyridin-4-yl](CH$_2$)$_5$* | Na (2) | / | 1183 | 7.53 | 1 |
| 13 | —Ph-4-O* | —CH$_3$ | H | CH$_2$COOH | *(CH$_2$)$_5$N{(CH$_2$)-[4-N(CH$_3$)$_2$Ph]}(CH$_2$)$_5$* | Na (2) | / | 1225 | 17.89 | 2 |
| 14 | —Ph-4-O* | —CH$_3$ | H | CH$_2$COOH | *(CH$_2$)$_5$N[(CH$_2$)$_2$N(CH$_2$CH$_3$)$_2$](CH$_2$)$_5$* | Na (2) | / | 1191 | 8.18 | 1 |
| 15 | —Ph-4-O* | —CH$_3$ | H | CH$_2$COOH | *(CH$_2$)$_3$N[(CH$_2$)$_2$]$_2$N(CH$_2$)$_3$* | HCl (2) | / | 1105 | 7.32 | 1 |
| 16 | —Ph-4-CONH* | —CH$_3$ | H | CH$_2$COOH | *(CH$_2$)$_2$OP(O)(OH)O(CH$_2$)$_2$* | Na (3) | / | 1147 | 9.98 | 2 |
| 17 | —Ph-4-CONH* | —CH$_3$ | H | CH$_2$COOH | *(CH$_2$)$_2$O(CH$_2$)$_2$O(CH$_2$)$_2$* | Na (2) | / | 1107 | 11.84 | 2 |
| 18 | —Ph-3-CONH* | —CH$_3$ | H | CH$_2$COOH | *(CH$_2$)$_2$O(CH$_2$)$_2$O(CH$_2$)$_2$* | Na (2) | / | 1107 | 6.29 | 1 |
| 19 | —Ph-3-CONH* | —CH$_3$ | H | CH$_2$COOH | *(CH$_2$)$_2$OP(O)(OH)O(CH$_2$)$_2$* | Na (3) | / | 1143 | 5.67 | 1 |
| 20 | —NHCOPh-3-O* | —CH$_3$ | H | CH$_2$COOH | *CH$_2$CONH(CH$_2$)$_2$NHCOCH$_2$* | Na (2) | / | 1165 | 5.95 | 1 |

The results of pharmacological tests in vitro and in vivo carried out with a view to determining properties of the compounds of the invention are listed below:

| Compound | % activation with respect to FGF2 (in vitro) | EC50 |
|---|---|---|
| 2 | 44% | EC50 < 1 nM |
| 3 | 74% | EC50 < 1 nM |
| 4 | 57% | EC50 < 1 nM |
| 5 | 30% | EC50 < 100 nM |
| 6 | 29% | EC50 < 100 nM |
| 7 | 28% | EC50 < 100 nM |
| 8 | 42% | EC50 < 1 nM |
| 9 | 28% | EC50 < 100 nM |
| 10 | 41% | EC50 < 1 nM |
| 11 | 63% | EC50 < 1 nM |
| 12 | 42% | EC50 < 1 nM |
| 13 | 23% | EC50 < 100 nM |
| 14 | 62% | EC50 < 1 nM |
| 15 | 24% | EC50 < 100 nM |
| 16 | 82% | EC50 < 1 nM |
| 17 | 44% | EC50 = 10 nM |
| 18 | 85% | EC50 < 1 nM |
| 19 | 35% | EC50 = 3 nM |
| 20 | 61% | EC50 < 3 nM |

In Vitro Angiogenesis Model

The products are tested for their ability to cause rearrangement of human venous endothelial cells (HUVECs) on matrigel (Becton dickinson 356230) diluted in collagen (rat tail collagen, type I: Becton dickinson 354236). After 24 hours, the cells are observed under a microscope with a ×4 objective and the length of the pseudotubules is measured by means of an image analyser (BIOCOM-logiciel Visiolab 2000).

For the in vitro angiogenesis test, the compounds of the invention demonstrated a specific activity between $10^{-6}$ M and $10^{-12}$ M. By way of example, compounds 3 and 16 are active at a concentration of 10 nM on the in vitro angiogenesis model.

Sponge Angiogenesis Model

The sponge angiogenesis model is an adaptation of the technique of Andrade et al. [Andrade S P, Machado R., Teixeiras, Belo A V, Tarso A M, Beraldo W T—Sponge-induced angiogenesis in mice and the pharmacological reactivity of the neovasculature quantitated by fluorimetric method, Microvascular Research, 1997, 54: 253-61.]

The mice used are BalbC females from Charles River Laboratory, 7 to 10 weeks old. The animals are anaesthetized by intraperitoneal injection of a xylazine/ketamine mixture (1 mg/kg each in 0.9% NaCl). The animal's back is shaved and disinfected with hexomedine. A subcutaneous 5 ml pocket of air is made on the animal's back with sterile air. An incision is then made (approximately 1 cm) on the top of the animal's back in order to implant the sponge in the pocket. The biocompatible cellulose sponge (Cellspon, Interchim, 10 mm in diameter) was sterilized beforehand (autoclave 20 min at 120° C.) and is impregnated with 50 µl of sterile solution containing the test product. Suturing is performed by inserting two 9-mm stainless steel autoclip staples (Subra). The wound is again disinfected with hexomedine. The animals are housed in individual cages throughout the duration of the experiment.

The test products are in solution in a PBS/0.1% BSA mixture: the recombinant human FGF2 (Peprotech) and the products of invention are placed in solution extemporaneously according to the concentration selected. On the two days following the implantation of the cellulose sponge, the test products in solution are reinjected directly into the implant through the animal's skin, after having disinfected the area with hexomedine.

On the eighth day after implantation, the mice are sacrificed with a lethal dose of sodium pentobarbital (CEVA santé animale, 10 mg/kg) administered intraperitoneally. The skin is cut out around the sponge (approximately 1 cm) and the sponge is separated from the skin by removing the connective tissue. The sponge is cut into 3 or 4 pieces and placed in a tube containing ceramic beads with 1 ml of RIPA lysis buffer. The lysis is performed by means of two cycles of agitation for 20 seconds (FastPrep® FP 120). After freezing of the supernatants at −20° C., the tubes are centrifuged at 8000 rpm for 10 minutes and the supernatants are removed in order to assay the haemoglobin.

To assay the haemoglobin, 50 µl of each sample are deposited in a 96-well plate, in duplicate. The range is prepared with human haemoglobin (ref H7379, Sigma®) in a solution of 4 mg/ml to 0.06 mg/ml in the RIPA lysis buffer. 50 µl of Drabkin reagent (Sigma®) are deposited in all the wells (range+samples). The plate is incubated for 15 min at ambient temperature, in the dark. The OD values are read on a spectrophotometer at 405 nm, using the Biolise software (Tecan, France). The Hb concentration in each sample is expressed in mg/mL according to the polynomial regression performed using the range.

By way of example, compound 4 is active at a concentration of 300 µM on the in vitro angiogenesis model.

The compounds of the invention exhibit an FGF receptor agonist activity. They induce receptor dimerization and, by virtue of their low toxicity and their pharmacological and biological properties, the compounds of the present invention represent a therapy of choice in pathological conditions for which FGFs have a positive effect, such as post-ischaemic revascularization, healing processes, and neuronal, muscle and bone repair and regeneration processes.

One of the applications of the compounds of the invention is treatment requiring an increase in angiogenesis, such as post-ischaemic treatment after occlusion of peripheral arteries or treatment of the consequences of cardiac ischaemia. The compounds described in the invention can be of use in the treatment of diseases associated with narrowing of coronary arteries and in particular in the treatment of angina pectoris or of thromboangiitis obliterans. Moreover, the compounds of said invention could represent a treatment of choice for compensating for a deficiency in angiogenesis in pre-eclamptic placentas. Through their anti-apoptotic activity on endothelial cells, the products of said invention could provide a treatment of choice in vascular improvement in patients suffering from vascular damage, and in particular patients suffering from ARDS.

Through their FGF receptor agonist activities and their abilities to induce angiogenesis and to activate mesenchymal cells involved in the phases of healing, the compounds of said invention would represent a therapy of choice for treating healing, in particular in elderly or diabetic patients. The compounds presented in the invention could represent a treatment of choice for muscle regeneration.

By virtue of the FGF receptor agonist activity, the compounds of said invention would represent a treatment of choice in the treatment of nociception, in the treatment of chronic pain and in the treatment of peripheral neuropathy, in particular in diabetic patients.

Through the FGF receptor agonist properties, the compounds of said invention could represent a treatment of choice in bone repair after fracture.

The compounds of said invention would represent a therapy of choice in the improvement of bioartificial pancreatic graft survival in diabetic patients and, more generally, in the improvement of graft revascularization and in graft survival.

Through their FGF receptor agonist activity, the compounds of said invention could provide a treatment of choice for hair follicle repair and protection and in the protection and regulation of hair growth.

According to another of its aspects, the compounds according to the invention are of use for the treatment of diseases requiring FGF receptor activation. A subject of the present invention is more particularly the use of a compound as defined above, for preparing a medicament that is of use in the treatment of cardiac ischaemia, the treatment of diseases associated with narrowing or obstruction of the arteries or of arteritis, the treatment of angina pectoris, the treatment of thromboangiitis obliterans, the treatment of atherosclerosis, treatment for inhibiting post-angioplasty or post-endoarterectomy restenosis, the treatment of healing, treatment for muscle regeneration, treatment for myoblast survival, treatment for sarcopenia, loss of functionality of the smooth muscles of the sphincters, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of pigmentary retinitis, the treatment of osteoarthritis, the treatment of pre-eclampsia, the treatment of vascular lesions and of acute respiratory distress syndrome, bone protection treatment, or treatment for hair follicle protection.

According to another of its aspects, a subject of the present invention is therefore the use of a compound as defined above, for preparing a medicament that is of use in the treatment of diseases requiring FGF receptor activation. A subject of the present invention is more particularly the use of a compound as defined above, for preparing a medicament that is of use in the treatment of cardiac ischaemia, the treatment of diseases associated with narrowing or obstruction of the arteries or of arteritis, the treatment of angina pectoris, the treatment of thromboangiitis obliterans, the treatment of atherosclerosis, treatment for inhibiting post-angioplasty or post-endoarterectomy restenosis, the treatment of healing, treatment for muscle regeneration, treatment for myoblast survival, treatment for sarcopenia, loss of functionality of the smooth muscles of the sphincters, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of pigmentary retinitis, the treatment of osteoarthritis, the treatment of pre-eclampsia, the treatment of vascular lesions and of acute respiratory distress syndrome, bone protection treatment, or treatment for hair follicle protection.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, and also at least one pharmaceutically acceptable excipient.

Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, can be administered in unit administration form, as a mixture with conventional pharmaceutical excipients, to animals or to human beings for the prophylaxis or treatment of the above disorders or diseases.

The appropriate unit administration forms include oral forms, such as tablets, soft or hard gel capsules, powders, granules and oral solutions or suspensions, sublingual, buccal, intratracheal, intraocular and intranasal administration forms, forms of administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following constituents:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating and/or preventing the pathological conditions indicated above, which comprises the administration, to a patient, of an effective dose of a compound according to the invention, or a pharmaceutically acceptable salt thereof.

The invention claimed is:

1. A compound of the formula:

in which $M_1$ and $M_2$, which may be identical or different, each represent, independently of one another, a monomer unit M; and L represents a linker group which links $M_1$ and $M_2$ covalently, wherein
monomer unit M is of formula (M):

(M)

in which,
* indicates the site of linkage between the monomer unit M and the linker L, $R_1$ represents
  a group —NHCOPhO*, such that the *-labeled oxygen atom is covalently bonded to linker L; or
  an aryl group or a heteroaryl group, said group being substituted with a group chosen from a divalent oxygen atom, such that the oxygen atom is covalently bonded to the linker L, and an amide group —CONH*—, such that the *-labeled nitrogen atom is covalently bonded to the linker L, $R_2$ represents an alkyl group, $R_3$ represents a hydrogen atom or a linear, branched, or cyclic alkyl group, and $R_4$ represents a hydrogen atom, an alkyl, or -alkyl-COOR$_5$ group, with $R_5$ representing a hydrogen atom or an alkyl group; and linker L is chosen from formula (A), formula (B), formula (C), formula (D) or formula (E):

(A)

(B)

(C)

(D)

(E)

wherein
* indicates the atom for connecting L with $R_1$,
n represents 0, 1, 2, 3, 4, or 5,
m represents 1, 2, 3, 4, or 5,
r represents 1, 2, 3, 4, 5, or 6,
$R_2$' and $R_2$", which may be identical or different, represent a linear alkyl radical having from 1 to 5 carbon atoms, and which can be optionally linked to form a ring,
$R_6$ represents a $(C_1$-$C_4)$alkyl group optionally substituted with one or more substituents independently selected from:
  an aryl or heteroaryl group, each optionally substituted with hydroxy or $NR_6$'$R_6$", where $R_6$' and $R_6$" are independently chosen from a hydrogen atom or a linear, branched or cyclic $(C_1$-$C_4)$alkyl group,
  a heterocycloalkyl group comprising at least one heteroatom chosen from a nitrogen atom and an oxygen atom, wherein the heterocycloalkyl group is optionally substituted with a linear or branched alkyl group,
  an $NR_6$'$R_6$" group where $R_6$' and $R_6$" are independently chosen from a hydrogen atom or a linear, branched or cyclic $(C_1$-$C_4)$alkyl group, and
  an —O—$(C_1$-$C_4)$alkyl group optionally substituted with a hydroxy group,
or a pharmaceutically acceptable salt thereof.

2. The compound according to claim 1, wherein $R_1$ represents a group —NHCO-PhO*, -Ph-O* or -Ph-CONH*, or a pharmaceutically acceptable salt thereof.

3. The compound according to claim 1, wherein $R_2$ represents a methyl group, or a pharmaceutically acceptable salt thereof.

4. The compound according to claim 1, wherein:
$R_3$ represents a hydrogen atom,
$R_4$ represents an -alkyl-COOR$_5$ group, wherein $R_5$ represents a hydrogen atom or an alkyl group, or a pharmaceutically acceptable salt thereof.

5. The compound according to claim 1, such that the monomer units $M_1$ and $M_2$ are identical.

6. The compound according to claim 1 chosen from the following compounds:
  2,2'-{oxybis[ethane-2,1-diyloxyethane-2,1-diyloxybenzene-3,1-diyl(2-methylindolizine-1,3-diyl)carbonyl(2,4-dioxo-1,4-dihydroquinazoline-6,3(2H)-diyl)]}diacetic acid;
  2,2'-{oxybis[ethane-2,1-diyloxyethane-2,1-diyloxybenzene-3,1-diyl(2-methylindolizine-1,3-diyl)carbonyl(2,4-dioxo-1,4-dihydroquinazoline-6,3(2H)-diyl)]}diacetic acid;
  2,2'-{ethane-1,2-diylbis[oxyethane-2,1-diyloxybenzene-4,1-diyl(2-methylindolizine-1,3-diyl)carbonyl(2,4-dioxo-1,4-dihydroquinazoline-6,3(2H)-diyl)]}diacetic acid;
  2,2'-{hexane-1,6-diylbis[imino(2-oxoethane-2,1-diyl) oxybenzene-4,1-diyl(2-methylindolizine-1,3-diyl)carbonyl(2,4-dioxo-1,4-dihydroquinazoline-6,3(2H)-diyl)]}diacetic acid;

2,2'-{butane-1,4-diylbis[imino(2-oxoethane-2,1-diyl) oxybenzene-4,1-diyl(2-methylindolizine-1,3-diyl)carbonyl(2,4-dioxo-1,4-dihydroquinazoline-6,3(2H)-diyl)]}diacetic acid;

2,2'-{hexane-1,6-diylbis[imino(2-oxoethane-2,1-diyl) oxybenzene-3,1-diyl(2-methylindolizine-1,3-diyl)carbonyl(2,4-dioxo-1,4-dihydroquinazoline-6,3(2H)-diyl)]}diacetic acid;

2,2'-{butane-1,4-diylbis[imino(2-oxoethane-2,1-diyl) oxybenzene-3,1-diyl(2-methylindolizine-1,3-diyl)carbonyl(2,4-dioxo-1,4-dihydroquinazoline-6,3(2H)-diyl)]}diacetic acid;

2,2'-({[2-(2-hydroxyethoxyl)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

2,2'-{(ethylimino)bis[pentane-5,1-diyloxybenzene-4,1-diyl(2-methylindolizine-1,3-diyl)carbonyl(2,4-dioxo-1,4-dihydroquinazoline-7,3(2H)-diyl)]}diacetic acid;

2,2'-({[2-(morpholin-4-yl)ethyl]imino}bis[pentane-5,1-diyloxybenzene-4,1-diyl(2-methylindolizine-1,3-diyl) carbonyl(2,4-dioxo-1,4-dihydroquinazoline-7,3(2H)-diyl)])diacetic acid;

2,2'-({[2-(4-methylpiperazin-1-yl)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

2,2'-{[(pyridin-4-ylmethyl)imino]bis[pentane-5,1-diyloxybenzene-4,1-diyl(2-methylindolizine-1,3-diyl)carbonyl(2,4-dioxo-1,4-dihydroquinazoline-7,3(2H)-diyl)]}diacetic acid;

2,2'-({[4-(dimethylamino)benzyl]imino}bis[pentane-5,1-diyloxybenzene-4,1-diyl(2-methylindolizine-1,3-diyl) carbonyl(2,4-dioxo-1,4-dihydroquinazoline-7,3(2H)-diyl)])diacetic acid;

2,2'-({[2-(diethylamino)ethyl]imino}bis[pentane-5,1-diyloxybenzene-4,1-diyl(2-methylindolizine-1,3-diyl)carbonyl(2,4-dioxo-1,4-dihydroquinazoline-7,3(2H)-diyl)])diacetic acid;

2,2'-{piperazine-1,4-diylbis[propane-3,1-diyloxybenzene-4,1-diyl(2-methylindolizine-1,3-diyl)carbonyl(2,4-dioxo-1,4-dihydroquinazoline-7,3(2H)-diyl)]}diacetic acid;

[7-({1-[4-({9-[4-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphonon-1-yl}carbamoyl)phenyl]-2-methylindolizin-3-yl}carbonyl)-2,4-dioxo-1,4-dihydroquinazolin-3(2H)-yl]acetic acid;

2,2'-{ethane-1,2-diylbis[oxyethane-2,1-diylcarbamoylbenzene-4,1-diyl(2-methylindolizine-1,3-diyl)carbonyl (2,4-dioxo-1,4-dihydroquinazoline-7,3(2H)-diyl)]}diacetic acid;

2,2'-{ethane-1,2-diylbis[oxyethane-2,1-diylcarbamoylbenzene-3,1-diyl(2-methylindolizine-1,3-diyl)carbonyl (2,4-dioxo-1,4-dihydroquinazoline-7,3(2H)-diyl)]}diacetic acid;

[7-({1-[3-({9-[3-(3-{[3-(carboxymethyl)-2,4-dioxo-1,4-dihydroquinazolin-7(2H)-yl]carbonyl}-2-methylindolizin-1-yl)phenyl]-4-hydroxy-4-oxido-9-oxo-3,5-dioxa-8-aza-4λ$^5$-phosphonon-1-yl}carbamoyl)phenyl]-2-methylindolizin-3-yl}carbonyl)-2,4-dioxo-1,4-dihydroquinazolin-3(2H)-yl]acetic acid;

2,2'-{ethane-1,2-diylbis[imino(2-oxoethane-2,1-diyl) oxybenzene-3,1-diylcarbonylimino(2-methylindolizine-1,3-diyl)carbonyl(2,4-dioxo-1,4-dihydroquinazoline-7,3(2H)-diyl)]}diacetic acid; and a pharmaceutically acceptable salt thereof.

7. A pharmaceutical composition comprising a compound according to claim 1, or a pharmaceutically acceptable salt thereof, and at least one pharmaceutically acceptable excipient.

8. A method of activating fibroblast growth factor receptor in a patient, comprising administering to the patient a compound according to claim 1.

9. The method according to claim 8, wherein the patient suffers from cardiac ischaemia, arteritis, arteriosclerosis, angina pectoris, obesity, diabetes, thromboangiitis obliterans, post-angioplasty restenosis, post-endoarterectomy restenosis, muscle injury, muscular dystrophy, myoblast survival, sarcopenia, nociception, chronic pain, peripheral neuropathy, bioartificial pancreatic graft survival, graft revascularization, retinal degeneration, pigmentary retinitis, osteoarthritis, osteoporosis, preeclampsia, vascular lesions, acute respiratory distress syndrome or alopecia.

10. A method of promoting angiogenesis in a patient, comprising administering to the patient a compound according to claim 1.

11. A process for preparing a compound according to claim 1, wherein:

(a)
a compound of formula (IX)

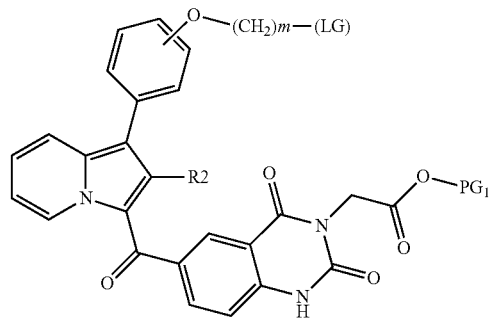

(IX)

in which m represents 1, 2, 3, 4, or 5, $R_2$ represents an alkyl group, $PG_1$ represents an alkyl group and LG represents a halogen atom or an activated hydroxy group, reacts with an amine $R_6$—$NH_2$ in the presence of a base to give a dimer of formula (XV):

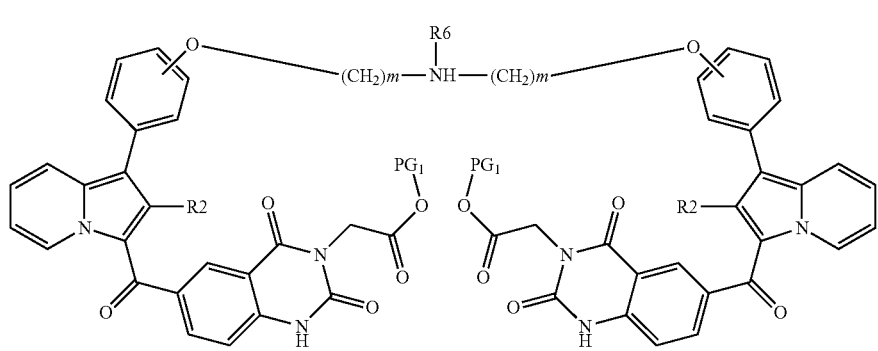

or (b) an amine of formula (XVI)

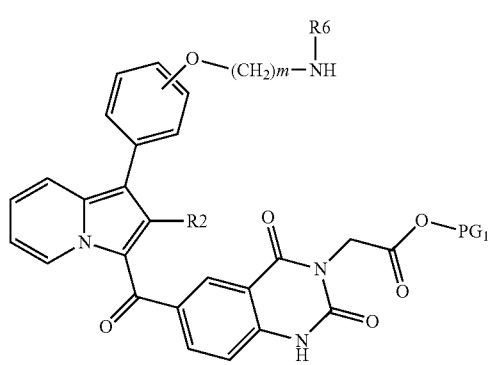

wherein $R_6$ independently represents a $(C_1-C_4)$alkyl group optionally substituted with one or more substituents independently chosen from:
  an aryl or heteroaryl group, each optionally substituted with hydroxyl or $NR_6'R_6''$ group, wherein $R_6'$ and $R_6''$ are independently chosen from a hydrogen atom and a linear, branched or cyclic $(C_1-C_4)$alkyl group,
  a heterocycloalkyl group comprising at least one heteroatom chosen from a nitrogen atom and an oxygen atom optionally substituted with a linear or branched alkyl group,
  an $NR_6'R_6''$ group, wherein $R_6'$ and $R_6''$ are independently chosen from a hydrogen atom and a linear, branched or cyclic $(C_1-C_4)$alkyl group, and
  an $-O-(C_1-C_4)$alkyl group optionally substituted with a hydroxy group, or a pharmaceutically acceptable salt thereof;
when present in excess, reacts with a stoichiometric amount of the compound of formula (IX) to give the dimer of formula (XV), and
the dimer of formula (XV) is saponified.

* * * * *